United States Patent
Ye et al.

(10) Patent No.: US 6,869,928 B2
(45) Date of Patent: Mar. 22, 2005

(54) ISOLATED HUMAN TRANSPORTER PROTEINS, NUCLEIC ACID MOLECULES ENCODING HUMAN TRANSPORTER PROTEINS AND USES THEREOF

(75) Inventors: Jane Ye, Boyds, MD (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 238 days.

(21) Appl. No.: 10/274,968

(22) Filed: Oct. 22, 2002

(65) Prior Publication Data

US 2003/0049793 A1 Mar. 13, 2003

Related U.S. Application Data

(62) Division of application No. 09/740,027, filed on Dec. 20, 2000, now Pat. No. 6,485,939.

(51) Int. Cl.$^7$ ................................................ C07K 14/00
(52) U.S. Cl. .......................................... 514/2; 530/350
(58) Field of Search ............................... 514/2; 530/350

*Primary Examiner*—Karen Cochrane Carlson
(74) *Attorney, Agent, or Firm*—Celera Genomics; Lin Sun-Hoffman

(57) ABSTRACT

The present invention provides amino acid sequences of peptides that are encoded by genes within the human genome, the transporter cofactor peptides of the present invention. The present invention specifically provides isolated peptide and nucleic acid molecules, methods of identifying orthologs and paralogs of the transporter cofactor peptides, and methods of identifying modulators of the transporter cofactor peptides.

4 Claims, 17 Drawing Sheets

```
   1 GTCTGTGGTC CTCTCTCGGC TCCTCGCGGC TCGCGGCGGC CGACGGTTCC
  51 TGGGACACCT GCTTGCTTGG CCCGTCCGGC GGCTCAGGGC TTCTCTGCTG
 101 CGCTCCCGGT TCGCTGGACG GGAAGAAGGG CTGGGCCGTC CCGTCCCGTC
 151 CCCATCGGAA CCCCAAGTCG CGCCGCTGAC CCGTCGCAGG GCGAGATGAG
 201 CGCGGACGCA GCGGCCGGGG CGCCCCTGCC CCGGCTCTGC TGCCTGGAGA
 251 AGGGTCCGAA CGGCTACGGC TTCCACCTGC ACGGGGAGAA GGGCAAGTTG
 301 GGCCAGTACA TCCGGCTGGT GGAGGTGAAC GGCGAAAACG TGGAGAAGGA
 351 GACCCACCAG CAGGTGGTGA GCCGCATCCG CGCCGCACTC AACGCCGTGC
 401 GCCTGCTGGT GGTCGACCCC GAGACGGACG AGCAGCTGCA GAAGCTCGGC
 451 GTCCAGGTCC GAGAGGAGCT GCTGCGCGCC CAGGAAGCGC GGGGCAGGC
 501 CGAGCCGCCG GCCGCCGCCG AGGTGCAGGG GGCTGGCAAC GAAAATGAGC
 551 CTCGCGAGGC CGACAAGAGC CACCCGGAGC AGCGCGAGCT TCGGCCTCGG
 601 CTCTGTACCA TGAAGAAGGG CCCCAGTGGC TATGGCTTCA ACCTGCACAG
 651 CGACAAGTCC AAGCCAGGCC AGTTCATCCG GTCAGTGGAC CCAGACTCCC
 701 CGGCTGAGGC TTCAGGGCTC CGGGCCCAGG ATCGCATTGT GGAGGTGAAC
 751 GGGGTCTGCA TGGAGGGGAA GCAGCATGGG GACGTGGTGT CCGCCATCAG
 801 GGCTGGCGGG GACGAGACCA AGCTGCTGGT GGTGGACAGG GAAACTGACG
 851 AGTTCTTCAA GAAATGCAGA GTGATCCCAT CTCAGGAGCA CCTGAATGGT
 901 CCCCTGCCTG TGCCCTTCAC CAATGGGGAG ATACAGAAGG AGAACAGTCG
 951 TGAAGCCCTG GCAGAGGCAG CCTTGGAGAG CCCCAGGCCA GCCCTGGTGA
1001 GATCCGCCTC CAGTGACACC AGCGAGGAGC TGAATTCCCA AGACAGCCCC
1051 CCAAAACAGG ACTCCACAGC GCCCTCGTCT ACCTCCTCCT CCGACCCCAT
1101 CCTAGACTTC AACATCTCCC TGGCCATGGC CAAAGAGAGG GCCCACCAGA
1151 AACGCAGCAG CAAACGGGCC CCGCAGATGG ACTGGAGCAA GAAAAACGAA
1201 CTCTTCAGCA ACCTCTGAGC GCCCTGCTGC CACCCAGTGA CTGGCAGGGC
1251 CGAGCCAGCA TTCCACCCCA CCTTTTTCCT TCTCCCCAAT TACTCCCCTG
1301 AATCAATGTA CAAATCAGCA CCCACATCCC CTTTCTTGAC AAATGATTTT
1351 TCTAGAGAAC TATGTTCTTC CCTGACTTTA GGGAAGGTGA ATGTGTTCCC
1401 GTCCTCCCGC AGTCAGAAAG GAGACTCTGC CTCCCTCCTC CTCACTGAGT
1451 GCCTCATCCT ACCGGGTGTC CCTTTGCCAC CCTGCCTGGG ACATCGCTGG
1501 AACCTGCACC ATGCCAGGAT CATGGGACCA GGCGAGAGGG CACCCTCCCT
1551 TCCTCCCCCA TGTGATAAAT GGGTCCAGGG CTGATCAAAG AACTCTGACT
1601 GCAGAACTGC CGCTCTCAGT GGACAGGGCA TCTGTTACCC TGAGACCTGT
1651 GGCAGACACG TCTTGTTTTC ATTTGATTTT TGTTAAGAGT GCAGTATTGC
1701 AGAGTCTAGA GGAATTTTTG TTTCCTTGAT TAACATGATT TTCCTGGTTG
1751 TTACATCCAG GGCATGGCAG TGGCCTCAGC CTTAAACTTT TGTTCCTACT
1801 CCCACCCTCA GCGAACTGGG CAGCACGGGG AGGGTTTGGC TACCCCTGCC
1851 CATCCCTGAG CCAGGTACCA CCATTGTAAG GAAACACTTT CAGAAATTCA
1901 GCTGGTTCCT CCAAAAAAAA AAAAAAAAAA AAAAAAAAAA AAAAAAAA (SEQ ID NO:1)
```

FEATURES:
5'UTR: 1-195
Start Codon: 196
Stop Codon: 1215
3'UTR: 1218

FIGURE 1A

HOMOLOGOUS PROTEINS:
Top BLAST Hits:

```
                                                                    Score     E
gi|11424705|ref|XP_008188.1| solute carrier family 9 (sodium/hy...   806     0.0
gi|4759140|ref|NP_004243.1| solute carrier family 9 (sodium/hyd...   674     0.0
gi|11024674|ref|NP_067605.1| ERM-binding phosphoprotein [Rattus...   583     e-165
gi|2137012|pir||I46532 protein co-factor - rabbit >gi|687675|gb...    578     e-164
gi|6755566|ref|NP_036160.1| solute carrier family 9 (sodium/hyd...   573     e-162
gi|11431133|ref|XP_007931.1| solute carrier family 9 (sodium/hy...   300     5e-80
gi|2198849|gb|AAC63061.1| (AF004900) E3KARP [Homo sapiens] >gi|...    293     4e-78
gi|2047328|gb|AAB53042.1| (U82108) SIP-1 [Homo sapiens]              287     2e-76
gi|8918244|dbj|BAA97568.1| (AB026489) mSlc9a3r2/E3karp/Sip-1/Tk...    286     8e-76
gi|4759142|ref|NP_004776.1| solute carrier family 9 (sodium/hyd...   261     2e-70
```

BLAST to dbEST:

```
                                                                    Score     E
gb|BE543846|BE543846 601071529F1 NIH_MGC_12 Homo sapiens cDNA c...   1280    0.0
gb|BF033883|BF033883 601456275F1 NIH_MGC_66 Homo sapiens cDNA c...   1123    0.0
gb|BE253116|BE253116 601116638F1 NIH_MGC_16 Homo sapiens cDNA c...   1119    0.0
gb|BE259858|BE259858 601154263F1 NIH_MGC_19 Homo sapiens cDNA c...   1086    0.0
gb|BE379337|BE379337 601236458F1 NIH_MGC_44 Homo sapiens cDNA c...   1054    0.0
gb|BE697273|BE697273 QV1-CT0417-080800-305-e05 CT0417 Homo sapi...    897    0.0
gb|BE796344|BE796344 601591950F1 NIH_MGC_7 Homo sapiens cDNA cl...    893    0.0
gb|AA311728|AA311728 EST182668 Jurkat T-cells VI Homo sapiens c...    786    0.0
gb|AA402592|AA402592 zu47e08.r1 Soares ovary tumor NbHOT Homo s...    717    0.0
gb|AV733237|AV733237 AV733237 cdA Homo sapiens cDNA clone cdAAZ...    705    0.0
gb|N99821|N99821 za31h06.r1 Soares fetal liver spleen 1NFLS Hom...    695    0.0
gb|BE562329|BE562329 601344368F1 NIH_MGC_8 Homo sapiens cDNA cl...    661    0.0
```

EXPRESSION INFORMATION FOR MODULATORY USE:
library source:
Expression information from BLAST dbEST hits:
gb|BE543846|pacenta - choriocarcinoma
gb|BF033883|ovary adenocarcinoma
gb|BE253116| eye - retinoblastoma
gb|BE259858|brain neuroblastoma
gb|BE379337| endometrium, adenocarcinoma cell line
gb|BE697273| colon
gb|BE796344| lung small cell carcinoma
gb|AA311728| T-lymphocyte
gb|AA402592| ovarian tumor
gb|AV733237| pheochromocytoma
gb|N99821| Soares fetal liver spleen
gb|BE562329|lymph Burkitt lymphoma Expression information from PCR-based tissue screening panels:
Human leukocyte

FIGURE 1B

```
  1  MSADAAAGAP LPRLCCLEKG PNGYGFHLHG EKGKLGQYIR LVEVNGENVE
 51  KETHQQVVSR IRAALNAVRL LVVDPETDEQ LQKLGVQVRE ELLRAQEAPG
101  QAEPPAAAEV QGAGNENEPR EADKSHPEQR ELRPRLCTMK KGPSGYGFNL
151  HSDKSKPGQF IRSVDPDSPA EASGLRAQDR IVEVNGVCME GKQHGDVVSA
201  IRAGGDETKL LVVDRETDEF FKKCRVIPSQ EHLNGPLPVP FTNGEIQKEN
251  SREALAEAAL ESPRPALVRS ASSDTSEELN SQDSPPKQDS TAPSSTSSSD
301  PILDFNISLA MAKERAHQKR SSKRAPQMDW SKKNELFSNL (SEQ ID NO:2)
```

FEATURES:

Functional domains and key regions:

[1] PDOC00001 PS00001 ASN_GLYCOSYLATION
N-glycosylation site 306-309 NISL

[2] PDOC00004 PS00004 CAMP_PHOSPHO_SITE
cAMP- and cGMP-dependent protein kinase phosphorylation site 319-322 KRSS

[3] PDOC00005 PS00005 PKC_PHOSPHO_SITE
Protein kinase C phosphorylation site

Number of matches: 6
    1    138-140 TMK
    2    152-154 SDK
    3    262-264 SPR
    4    321-323 SSK
    5    322-324 SKR
    6    331-333 SKK

[4] PDOC00006 PS00006 CK2_PHOSPHO_SITE
Casein kinase II phosphorylation site

Number of matches: 5
    1    125-128 SHPE
    2    168-171 SPAE
    3    242-245 TNGE
    4    275-278 TSEE
    5    297-300 SSSD

[5] PDOC00008 PS00008 MYRISTYL
N-myristoylation site 204-209 GGDETK

FIGURE 2A

BLAST Alignment to Top Hit:
>gi|4759140|ref|NP_004243.1| solute carrier family 9
   (sodium/hydrogen exchanger), isoform 3 regulatory factor
   1 [Homo sapiens]
gb|AAC04572.1| (AF036241) Na+/H+ exchange regulatory co-factor [Homo sapiens]
gb|AAC52084.1| (AF015926) ezrin-radixin-moesin binding phosphoprotein-50 [Homo
   sapiens]
   Length = 358

Score = 674 bits (1720), Expect = 0.0
Identities = 340/358 (94%), Positives = 340/358 (94%), Gaps = 18/358 (5%)

```
Query: 1   MSADAAAGAPLPRLCCLEKGPNGYGFHLHGEKGKLGQYIRLVE---------------- 43
           MSADAAAGAPLPRLCCLEKGPNGYGFHLHGEKGKLGQYIRLVE
Sbjct: 1   MSADAAAGAPLPRLCCLEKGPNGYGFHLHGEKGKLGQYIRLVEPGSPAEKAGLLAGDRLV 60

Query: 44  -VNGENVEKETHQQVVSRIRAALNAVRLLVVDPETDEQLQKLGVQVREELLRAQEAPGQA 102
            VNGENVEKETHQQVVSRIRAALNAVRLLVVDPETDEQLQKLGVQVREELLRAQEAPGQA
Sbjct: 61  EVNGENVEKETHQQVVSRIRAALNAVRLLVVDPETDEQLQKLGVQVREELLRAQEAPGQA 120

Query: 103 EPPAAAEVQGAGNENEPREADKSHPEQRELRPRLCTMKKGPSGYGFNLHSDKSKPGQFIR 162
           EPPAAAEVQGAGNENEPREADKSHPEQRELRPRLCTMKKGPSGYGFNLHSDKSKPGQFIR
Sbjct: 121 EPPAAAEVQGAGNENEPREADKSHPEQRELRPRLCTMKKGPSGYGFNLHSDKSKPGQFIR 180

Query: 163 SVDPDSPAEASGLRAQDRIVEVNGVCMEGKQHGDVVSAIRAGGDETKLLVVDRETDEFFK 222
           SVDPDSPAEASGLRAQDRIVEVNGVCMEGKQHGDVVSAIRAGGDETKLLVVDRETDEFFK
Sbjct: 181 SVDPDSPAEASGLRAQDRIVEVNGVCMEGKQHGDVVSAIRAGGDETKLLVVDRETDEFFK 240

Query: 223 KCRVIPSQEHLNGPLPVPFTNGEIQKENSREALAEAALESPRPALVRSASSDTSEELNSQ 282
           KCRVIPSQEHLNGPLPVPFTNGEIQKENSREALAEAALESPRPALVRSASSDTSEELNSQ
Sbjct: 241 KCRVIPSQEHLNGPLPVPFTNGEIQKENSREALAEAALESPRPALVRSASSDTSEELNSQ 300

Query: 283 DSPPKQDSTAPSSTSSSDPILDFNISLAMAKERAHQKRSSKRAPQMDWSKKNELFSNL 340
           DSPPKQDSTAPSSTSSSDPILDFNISLAMAKERAHQKRSSKRAPQMDWSKKNELFSNL
Sbjct: 301 DSPPKQDSTAPSSTSSSDPILDFNISLAMAKERAHQKRSSKRAPQMDWSKKNELFSNL 358 (SEQ
ID NO :4)
```

Hmmer search results (Pfam):

| Model | Description | Score | E-value | N |
|---|---|---|---|---|
| PF00595 | PDZ domain (Also known as DHR or GLGF). | 58.9 | 2.4e-15 | 2 |

Parsed for domains:

| Model | Domain | seq-f | seq-t | hmm-f | hmm-t | score | E-value |
|---|---|---|---|---|---|---|---|
| PF00595 | 1/2 | 40 | 75 .. | 48 | 83 .] | 6.8 | 1.9 |
| PF00595 | 2/2 | 136 | 215 .. | 1 | 83 [] | 51.4 | 3.4e-13 |

FIGURE 2B

```
   1 GTGTTGTGAA AAAAAAGAGA AATCCCTGGC TCCTGGAGCT GGTGGGAGAC
  51 AAGATTAAGC AAACCTCCCC TGACATGTAT CCCTTTGACC CCAAGCTCTG
 101 CCTCCTCCCT GACCACCCAT GCCCTTTCCT TTAACTTCTC AAACAGATAC
 151 CAGGGCCTAA ACTGCTTTAC CTCCCCTCCT ACTGAGTCAG GTTAGGTGGT
 201 GGGAGGTCAC CCATTTCCGA GTTAAACCAA TGCAATATGA GTAAAACAAA
 251 GTCATGTGGG TATGTCTGGG GTAGAGAGAG GGGTAGCAAG TTCATGTGTC
 301 CTCCTTGGTC ACATATCTCC CAAAGCTCTG ATCCCTGCCA TGGGAAGTGG
 351 ACAGGAAACA TGAGGTCATG ACCTGCAGGC ATCTTTACTG CAGCTCTGCC
 401 GGCCTGGAGG GGGAGAGGGG GAGGAAGAAG TATGCGCTGC ACATTTCTGA
 451 GGCTACTGCA TTTGCTTTCA AGGCAGAAAT CTTGCTCTGA GCAGTCAGCG
 501 GCTCCAGTTT GGGCCCGATA AGGAAGTTCT CCGTGGCCTC CCTCAGGCAG
 551 AGCAGGGAGG AGGCTGACAT TGCCAGTCTC TTCTGGGGCC CAAGGCAGGT
 601 TGCAGGAGAT CCAATCCCAT AGACAGCTCT GGGCCTCTTG CATTTGAGTT
 651 TTTCAGAATT AAACTGCAGT ATTTTGGAAA GCACATCCTG TCCACTGTTT
 701 CTTTGAAGTG AGTGGGGGGG GGGGGTCTTG TTGAAGGAAT TGTCATTCAC
 751 TGCCAAAATC ATTCCATCCT CCTTCCTCAG TGTCTGTCCT CAGATGGTCA
 801 GCTCCCCGCT CAACAGACTG TCTCCCGCCT CTGTGACCAG CCTCTCTTTG
 851 GCAAGAGGGA GCTAGAAGGC TTTACAGTCC TAATCATTTT TCTGTTGGAA
 901 AAAAAAAAAA AAAACCAAGG CTCCTTTCCC TGTGGCGTGT ACCCAGAGGT
 951 TGATTACCTG AGTCTGTCCT GCCTCTCCCC ACCCACCTC CCTAGCCAAA
1001 CGCTGCTGCC AAAGCCCACG CTATTGCCCT AGATGGCCTG TCTTCAGCGG
1051 GCTGCCCCTC GAGGTCCCAG GCTCTCCGCG GAGCCCTCAC CTTCCCAGCA
1101 GGGATCAGAA CCTGCACTCC TCTATGCGAG TCCTGGGACA GCACAAAGTG
1151 GATTAGGGTT AGGGTTCCCA CAAACGGAAA AATGTTATTC AAACAACTCT
1201 GTAGGGTCCG AGGAGGCCCT CCGTCTTAAT TCTCGAGACT GACCGGCCCT
1251 CGCTGCCCCG AGCGGGAGCA GTTGCCCCGG CAACAGCCGC TCCCTCTCAA
1301 CTGGAGCTGC ACCCAGGCTT TGGCTAAAGG CTGTTAAAAC GTTGGCCAGG
1351 TGCGGAGGCT CACGTCTGTA ATCCCAGGGC GGATCACCTG AGGTCAGGAG
1401 TTTGAAACCA TCCTGGCCAA CATGGCGAAA TTTCGTCTCT ACTAAAAATA
1451 CAAAAATTAG CGGGGCGTGG TGGTGCGCGC CTGTAACCCC AGCTGCTCGG
1501 GAGGCTGAGG CAGGGGAATC GCTTGAACCC GGGAGGCGGA GGTTGCAGTG
1551 ATCCGAGATC GCGCCACGGC AGTCCAGCCT GGGCGACAGA GCGAGACTCC
1601 GTCTCAAAAA AAAAAAAAAA AGTTAGGGTC CTTTACCCGA GGGCCGGCTT
1651 TCCTCACTCC CCGCCACAGG TAGGGGAAAC CAGGCCGGAG CCGGCGGGCC
1701 CACCCGCCCA GAACCGGGAA TTCGGCGAGC CCGCCCCTG CCACCCCAGC
1751 GCCGGCCGCT CGGTAACAAA CACTTCCACT TCCTGAGCGC TAGTCTTCGC
1801 CCGCCGCGGG CGCCGCGCC GAGCGCAGGC CCCGCCCCGC GCGTTCCCAA
1851 TGGCCGGCGC CGTTCACCCG GCCGGAGCGC CCAGGCCTGC AGCCCCCTAT
1901 TGGCCCGCGG GAGGTCCCCA CCCTCAGCGC GGCCCCGCCC CCGGGGTAAG
1951 GAGCCGGGGC GGACTCTGGG ACGCTCAGAC GCCGCGCGGG GCGGGGATTG
2001 GTCTGTGCTC CTCTCTCGGC TCCTCGCGGC TCGCGGCGGC CGACGGTTCC
2051 TGGGACACCT GCTTGCTTGG CCCGTCCGGC GGCTCAGGGC TTCTCTGCTG
2101 CGCTCCCGGT TCGCTGGACG GGAAGAAGGG CTGGGCCGTC CCGTCCCGTC
2151 CCCATCGGAA CCCCAAGTCG CGCCGCTGAC CCGTCGCAGG GCGAGATGAG
2201 CGCGGACGCA GCGGCCGGGG CGCCCCTGCC CCGGCTCTGC TGCCTGGAGA
2251 AGGGTCCGAA CGGCTACGGC TTCCACCTGC ACGGGGAGAA GGGCAAGTTG
2301 GGCCAGTACA TCCGGCTGGT GGAGCCCGGC TCGCCGGCCG AGAAGGCGGG
2351 GCTGCTGGCG GGGGACCGGC TGGTGGAGGT GAACGGCGAA AACGTGGAGA
2401 AGGAGACCCA CCAGCAGGTG GTGAGCCGCA TCCGCGCCGC ACTCAACGCC
2451 GTGCGCCTGC TGGTGGTCGA CCCCGAGACG GACGAGCAGC TGCAGAAGCT
2501 CGGCGTCCAG GTCCAGAGG AGCTGCTGCG CGCCCAGGAA GCGCCGGGGC
2551 AGGCCGAGCC GCCGGCCGCC GCCGAGGTGC AGGGGCTGGG CAACGAAAAT
2601 GAGCCTCGCG AGGCCGACAA GAGCCACCCG GAGCAGGTAA GCGGGGCCCG
2651 AGCCGCGCAG GCTGGCATGG AGTGGGAGGA GGATCCGGAG AGACCCAGGT
2701 GCCCCGGCCG TCCAGCCCCG CGCCCGCCGT CGTTTTCTG AAACTCGAGC
2751 TGCGAGGGGG AGACCGCTTC CGCCCGCCGA CCAGGCGCCC TGACACATCC
2801 TAGGCAGGCC TGGGGCTGCG TCCCGCGACC TCCTCTCCTT CCCAGGCTGT
2851 GCTGGGAGCT TGAGCGCCTT TGCCGCCTGC ACCTCTTGTT CCCTGGCCTT
2901 TGGGAGGGCG GCGCAGGGGA ACCCAGCCCC CTTCCCTCGG GTCTGTGGGT
2951 GTCTGCTCCC GTTCCTCGGA ATCCCCCAAT CCTGCTCCTT CCCTGGTGCC
3001 CTCTCCTCGT TCACCCCAGT CCGCAGATGG GCCGGGGAGA AAGGGCTCTC
3051 CGCCCAGAG GTGCCAGCTT CGCCCGCCAC TCCTACTTCA AAAGCTAGAG
```

FIGURE 3A

```
3101  GAATAGCATT ACTCCTCCTG TGTGGAGCCC CGGCGCGAGG AGGCCCTCTC
3151  CGCAGCCCGC CGGTGTGTGT CCTGAACTTC AGTCCTGCTG GACTTCATCC
3201  TCCCGGAGTC CTGTGTGACT TCTAAGGGAG AGGAAGCCCC ACCATCTCAG
3251  GGCGGTGTGG GGGTTGCCTG GCAGGGAGGA GGAGCCAAGG CATCTCGGAG
3301  TGGTGGTTCT GCCACCTCAG AGGATTTACG ATTCTCAGGA ATGTGAAGAG
3351  TAAGCGCCTA GAACTGTATC TGGGAGGGAA GGGGAAAGAC CTTGGAAGAA
3401  GAAAAAGATG GCCATGGGGA GGAGAGAGAG CTCCTGGGGC TCACGGCCCT
3451  GTGTGCGCCA GCGGAGCTCA CGGTGAGCCG GTGGTCTTGC CCTGGCCTTG
3501  CCATGGTCAC TCTGGTGCCC ACACAGCCAG CAGGCCGGTT GCTTTTTGCC
3551  CATGTTTGGT GTTTGCCCAT GGGATCCCAG TTTGGATCAG CTGCAAGAGG
3601  GGCAGCTGGC AAAATAGGAG TTGTGCTGAG CCTCCTGTCC CCAGAGAGTG
3651  GAGTGGTGCA TTGTGTAGGG CAGGGCGTGA GCCTCCCAGG ACCCCTTCAG
3701  CTTGCACCAC CAGCTCTCCC TGGTGGCAGT GTCTGATGGG AGTGTCCGTG
3751  GGGCTACGAG GAGCCTCCTG GACAGAGAAA GGGCACAGTT CGGCATTAAG
3801  GTAGAAGGCA AAGCCCTAGA GGATCAACTG GTTTGGTGGA AGTGAGGTCA
3851  CCAGAAGCCC TGTCCAGCCA GAGCTGGGTG CTGGGAATGC CAGGGCCACC
3901  AGGCTCCCAC TTCCTGCCCC TGCCAAGCTG GCATTGGCAA GGGGAGGGGG
3951  AAGGGATCTG AGCACCCGGA GCAAGGAGGT TGATGCCAGG GAGTTGGGGC
4001  CGATGATCTC CAGTCCCAGG CAGAAATCCA GTGTGAACTT TGTGCTGAGT
4051  CCATCGATCG ATTTGACATT CTTTTTTTTT TTTTTTTTG GACTTTGGCA
4101  CCCACACAAA TACCCACCCA CCCCCACCCC CCACAAGTTG CAGTCTCGTT
4151  CAGCTCCTCC CTTTGCCCTT TTGGTTATGC TGCTGGGTGC CAGAGGGCCT
4201  GGGAGGCGAA CGTGGAGGCC TGGCATAGCA CACGTGCGCA AAGGCAGCAG
4251  CTTTGAGCTT CCTGGGTGAG CACAGACTCA GTATTCCTGC ATGTTTTGGA
4301  GGGACACCTA CATTTGTGTG TACTTTGTTA GGCCAGGAGA TGAGAGGAGA
4351  GCCACCAGCA AATCCTGGGG ACACCATCAC CAGCCAAGTC CCAGGACTTC
4401  TGAGTTCTGG TTCTCCCATC TGTGAGATGG AGGCATTGGG CGATGTGATG
4451  CCTGCCTTCT CTAGAATTAT AGAAATGACG TGAAGCACTT GAGCCCCTTA
4501  CTAAATGCTG AACTGCACTC CTTCATGCCT GGCGTTTGAA TCCCAGCTCC
4551  TCTAAACTGA CTCCTAGTCA ACACCATTGA GTCCTTCTAG CAGAAAATCC
4601  TCTCCTCTCA ATCCTGTGTG TTGAGCATAC AGACACCCAT GTGGTTATTA
4651  GAAAAAATGT TAACAGACAT TGTAAGAGTT CGTTTTTCTA AAACACACCC
4701  GTTTCCTACA TAAAGCATCA AATGGAGGTT TGCCAATTCG TTTTAGTCTG
4751  AATTTGTGTG CAAGGTGGGG CTGTTCCCTT GTCTTCATTA GCCCTCCACT
4801  TACTAAGTGA TGATATCAGT GGAAAAGTGT GGCGCAGAGA GTGGTTGGCT
4851  GGGTGGCCTC TGGCTGGGAA GACCAGCTGT GTCCAGAACC ACTCAGGGCA
4901  GAGGCTGAGG GGTGCCTGTA ACACTGGCCA TCCCGCTGG GGAGTCTAGG
4951  CCTAAGGAGG TGGAAGTGGC TCTCCAGCTC TGCCCACCGG CTTTGCTTTG
5001  TGGATGGCCT TCCCCGCCTG CCCCGTGGGG AGAGAGGAGC AGCAAGACCC
5051  GCCCTGCTGT TCCCCTGCTT AAAGCCCTCC TCCCCCCATT CACCACCAGT
5101  CACAGGATGA GGCCTAAACC CTTGAGTCTG GGTTCAGAGT GCCGGCCGGG
5151  CAGAGCCGAG CCAGCTCAGC TGTACTAGCC AGGCTGTGCG AAGCCAAGTT
5201  ACCTCACCTC TGTAAGCCTC CATTTCCTCT TGTGTAAGTT GGGGGTTATG
5251  GCAGCTACCT CGGAATTGCA TGAGGCTGTG TGTAAAGCAC GTAGCTCAGT
5301  GCCTGGCACT GAGTCCAGGC TCAGCCAGCC TTTGCAGTTG GTATTGGAAT
5351  GAATACATAT TTCATAGTGA TCATTGCACA CCTATCATGG GGCAGCTAGC
5401  GCTGGGTCAG CCTGCCTAGT TGGGCAAATG CCACTGTGGC CAAGCCTGGC
5451  ACACAGTCAG TGCCTGATCG ATGGTCACTG TGGGTTAAGA ATGATACGTT
5501  GTGGCCAGGT GTGGTGGCTC ACACCTGTAA TCCCAGCACT TTGGGAGGCC
5551  AAAGTGGGAG GATCGCCTGA GCCCAGGAGT TTGAGACCAG CCTAGGCAAC
5601  ATGACAAGAC CCTGTCTCTA TTAAATTTTT TCTTTTTTTT TTTAAGAGT
5651  TATATGCTGT TCCATGGCCC TTCTCCATCT GGCAGCCTGT TCTCACCACT
5701  GCCTCCCTAC CCCCAAAACC ACACCCAGGG TCCGAATTCC CCTCTAACCT
5751  CTAAGCCTTC ACACCCTGAC ACTTCTGTCC CCTCCCAGGG AGCCTGTCCT
5801  TAATCCAGTA GGCAGAGTTA GCATTTCCTT TCCTTCACTT TTTTTGTTTT
5851  TGTTTTTGTT TTTGTTTTTT TTGAGACAGA TTCCACCCAG GCTGGAGTGG
5901  TGTCGCAACC TCGCCTCGCT GCAGCCTCGA CCTCCAGGGC TCAATCGATC
5951  CTCCCACCTC ATTCTCCCTA GTAGCTGGGA CTACAGGCAT GCACCACTAT
6001  TCCCAGCTAA TTTTTAAATT CTTTGTAGAG ATGGAGTTTC ACCGTGTTGC
6051  CCAGGCTGGT CTTGAACTCC TGGGCTGAGG TGATCTGCCA GCCTCGGCCT
6101  CCGCCTCCTC TTTGTCCTTA CATCTTTTAT CGCTCTAAAC ACACAATATT
6151  TTAATCATCT GTTTGTGACC TTTTTCTCCA CTACGTGGTA AGCCCAAGGG
```

FIGURE 3B

```
6201  CATCAACTGT GGCCTATTTG TGTTTCTATC CCCAGCGCTG TCCTTGGCAC
6251  ATGGTAGGGA GGCTCTCAAA AACAGTTTTT GAATTAATGA ATGAATATAT
6301  AACAACAGTC AGGGACCTTT GTCCTCATTC AGCTCATCCC GCCCCGCCCA
6351  GAGATTGGAA TTCCAGATAG AACCTACCCA CTCTTCTTTC TTGCCTGCTA
6401  GCAGCTTCTA TTTGAAAACT AGAAAGCCAA AAGTCCAGGC TTTGGGGTCA
6451  GCCAGATCAG TGTTTGAATC CCAGCTCTGC CGTGTGCTGG TTCTGGGATC
6501  CTGGGAGTTC ATTTTTCCCT GCAACCCTCA GCCTCCACCT CTGTGAAAGG
6551  CACTGCCTGC AGGGTTATTG GGAAGATTTG GTGGCATGAC AGGTTTGTAA
6601  ATGAAAGTGC TAGTTTGGGG TGTTTCCTGC CAGCCCTGAC CCTGATCCCA
6651  GAGTCAGAGT GCAGGCACCC CAGGGAGCAA GGTGGGTGGT GGGGCACAGT
6701  TAGCTGGAGG GCCATCAACC TCTTTCCCAG GGCGGGCGGG CCATTTTACA
6751  CCAACCAAGT TGGAGCTCTG GTAGGGCAGA ACAGAGCTTG AGCTGCTGGG
6801  TGTTTGGATT TGAAATGGAC AGGGTATGTG ATTGTTTGTG TGTTGGGATC
6851  TCTTTCTTTG CTGGCAAAAC AGTGTAGCCC CTGGTTCTTA CCTTCAAGCT
6901  CCTGTTAACT CAGTAATTCT GGAGATGATT CTCTTGGAGA TAGATGGGGG
6951  CTTCCTGGCC GGGCGCAGTG ACTTGTGCCT GTAATCCCAT CACTTCGGGA
7001  GGCTGAGGCG GGAGGATCGC TTAAGCCCAG GAGTTTGAGA CCAGCCTGGG
7051  CAACATAGTG AGACCTCGTC TCTACCAAAA AAACAGGGGG AGGGGGGTGA
7101  ATGGGGGCTT CCTTCTCAAG GAACTCCATA TGTCTAGATG GGGTCCTTCT
7151  CCCCTTTCCC AGATGTCCCA TCTCAATGGT CCCTGGGAAA GTGGGGTGGG
7201  AAATTAATAA GAAACTCAGG CCAGGCACGG TGGCTCACGC CTGTAATCCC
7251  AGCACTTTGG GAGGCCGAGG CGGGTGGATC AGTTGAGGTC AGGAGTTGAG
7301  GTCAGGAGTT CAAGACCAGC CTGGCCAACA TGGTAAAAAC CCATCTCTAC
7351  TAAAAATACA AAAATTAGCG AGGCGTGGTG GCAGGTGCCT GTAATCCCAG
7401  CTACTCGGGA GTCTGAGGCA GGAGAATGGC TTGAACCTGG GAGGTGGAGG
7451  TTTCAGTGAG CCGAGATCGC GCCACTGCAC TCCAGCCCGA GCAGCAGAGT
7501  GAGACTCATC TCCAAAATAA AAAAAAAGA AAGAAGAAGC TCAGCCGAGG
7551  TCTTGTTGGT GCTGCAGGAC TCTTTACAGG GAGAAACCAG AGCTCTAGAC
7601  CCCAATAACA AATGTTCCTC TGTTTTCGTT GCTCTAAGAT AGAGTGGCCC
7651  TACCTGGAAG GAAACAGGTT TGTACAGTGC CTTTAGGCAC TCTACCTATG
7701  ACATAAAGAT GTTGACATGC ATTTCTTTCT TTCTTTCTTT CTTTCTTTCT
7751  TTTTTTTTTT TTTTTTTTT TCCTGAGACA GTCTTGCTCT GTTGCCCAGG
7801  CTGGAGTGCA GTGGTGTGAT CTCGGCTCAC TGCAACCTCC GTCTCTCAAG
7851  TTCAAGCAAT TGTCCTGCCT CAGCCTTCCA TGTAGCTAGG ATTACAAACA
7901  CCCGCCACCA CACCCTGCTA ATTTTTGTAT TTTTAGTAGA GACGGAGTTT
7951  CACCACGGTG GCCAGGCTGG GTGGCACCTG TCACAACACC CTGCTAATTT
8001  TTGTATTTTT AGTAGAGATG GGGTTTCACC ACATTGGCCA GGCTGGTTTC
8051  AAACTCCTGA CCTCAGGTAA TCCACCTGCC TCGGTCTCCC AAAGTGCTGG
8101  GATTATAGGC ATGAGCCACC ACACCCAGCC AATATGCATT TCATTGTCCC
8151  CCAGACAAAT TAGCTATTGT TTTCTCTATT TTGTAGGTTG ACAGTAAGTG
8201  TTCAATACAT GATAGCTACT ATTTGTGTCT AGCACTGTGC TAAGTACTAA
8251  CCTTGCCTGT CTCATTTAAT CCACATGACC ACCAGTGAGG CAGATATTGG
8301  CCCCATTCTC TGCCTATGGA GGCTGAGGCT TGATCAGTTA AGGTGGCCAT
8351  GGCGGGTCCC AGGACTCTGA GCTAGCGACT CCTCCCACAC AGCGCAGGGG
8401  TGTGTCTTGG AACCCAACCC TCTGACTCTA GTGCCTGCAC AGCCATTTGG
8451  CCACATGAGT AGGCTGTGCT TGAAGCCTGA CTCTGCCAGG TGTTTCTGCC
8501  CATCATATTC TGAGCCACAG CTGGACCATC ACAGTGGTAT AAATTCAGGC
8551  TGCTTGAACT GGCTTCCTGT AAGGATCCAG GGCTTCCAGG TGCTCCTGTC
8601  CCTAGCAGGG CATCCTTGCA GTGCCTCAGC CCATAAGTGG CAGGCTCCTG
8651  TCCCCATCCC TTCTCACGTG ATGTGATAGG TCAATCTGGA ATCTGGTAAC
8701  CAAGTATCTA CCCCCGCCCT CACTCCCCAG AACCTGCACA GAGAGCCCCC
8751  CTCAAGGGTG GTCTTCACTG TTGACCGAAG CCTTCCCCTC ATGGTAGGAC
8801  AACTCACCAT GTCCCAGAC TCCTAGGCAA TGTTTAGGTC CCTAGGCCCT
8851  AGAAAAGGAC AAGAGTTACA GATTCCCTGA GGTCCAGGTC ACCTCGGGGT
8901  GGTGTGGGAA CACACAGAGA ATGCTGGCCA GGTTCAAGTC CCACTCACTG
8951  CTGGGTGCTG AGAGCTCTGA ATTCTCCGAG ACAGGCTGCA GCCTCTCCCT
9001  GTGCTAAGGT CAGGGGAACA GCAATGGCCA GGGGTATTTA GAGGAGTGTG
9051  TTTGGGGCAG TCTCAGGCAG CACAGGTCTG TGCTGTCCGG GCAGCAGCCA
9101  CCAGCTTCGC GAGGCTCCCG GGCACTCGAG ATGTGCTGGT CCACATGCAG
9151  ACGTGCTGTG TGTGCAAAAT GCACACCAGA TTTTGAAGCC ATTGTACAAA
9201  TAAAGGATG TACAATAGCT CAATTGTTAA AAATGGATTA CACATTGAAA
9251  TGATAATATT TTGGGTACAT TATGTTAAAT AAAATATTCA ATTCTACTAT
```

FIGURE 3C

```
 9301  TTTTCCTGTT TTTTTTTTTT TTGGAGGCAG AGTCTCGCTC TGTTGCCCAG
 9351  GCTGGAGTGC AGTGGTGCGA TCTCGGCTCA CTGCAAGCTC CACCTCCCAG
 9401  GTTCAAGCGA TTCTCCTGCC TCAGCCTCCC AAGTAGCTGT GCACCACCAC
 9451  GCCCAGCTGA TTTTTGTATT TTTCTTTTTT AGTAGAGATA GGGTTTCACC
 9501  ATGTTGACCA GGCTGGTCTC AAACTCCTGT GCTCAAGTGA TCCACTTGCC
 9551  TCGTCCTCCC AAAATGCTGG GATTACAGGC ATGAGCCACC ACACCTGGCC
 9601  TATTTTTCTT TTCTTTCTTT CTTTCTTTTT TTTTTTTTT TTTTTTTGA
 9651  GACGGAGCCT TGCTCTGTCA CCCAGGCTGG AGTGCAGTGG CGTGATCTCG
 9701  GCTCACTGCA ACCTCCGCCT CCTGGGTTCA AGCGGTTCTC GTGCCTCAGC
 9751  CTCTGGAGTA GCTGGGACCA CAGGTGTGCA CCACCACATA TGTCTAATTT
 9801  TCATATTTTT AGTTGAGACA GGGTTTCACC ATGTTGGCCA TGCTGGTCTT
 9851  GAACTCCCGA CCTCAGGTGA TCCACCTGCC TTGGCCTCCC AAAATGCTGG
 9901  GATTACAAGT GTGAGCCACT GCACCCGGCC TATTTTTCCT TTTTCAAATG
 9951  TGATGACTAG AAAATCTTAC ATTCCACACA TGGCTGGCAT TATATATCTA
10001  CTGGACAGTG CTGCTCTGGA TCTGAGCTCA AATCCTGCCT TTGCCCGTCA
10051  GCCATGTGTA CTTGAGCAAC TGACTCCAGC TTTTTGAAGC TGGGTTTCCT
10101  TTTCTGTGAA ATGCTGGCAA TAATACTTTC CTTTTAGGAC TATAATTGGC
10151  TCTTAAGAAG AAAACACATG TAAAGAGCTC GGTGCCTAAC ACATAGTAGG
10201  TGTTCAGTAA ATAGCAGCTG CTATTTGTTA CTTCAGTGTT GAGCCCCAAT
10251  TTCACAAGCT CCTTGAAGGT TCTTAATAGC CCCTTGGGAC AACCCCTGGG
10301  GGTTAAATCT AGAGACTTCT GGGAGGAGGG TGAGGGATGA GGAAGGATGC
10351  AGCAGGGAAG GCATGGGGCG GCCAGCCCTG GATGGTGTCC AGCCGGGCTG
10401  CAGCCCAGGT ACCAGCCTGC TCCATCCCAG GCTTGCCCAG CCCTGCAGAG
10451  ACCTGAGCCA GACTCTGCCC CCTCTTGCCC CCGTGGGTCT CCATGGCTGG
10501  CACAGGGAGA AGAGGTTACT AGCCAGAAGG AGAACCTGTT TCAGACCTCT
10551  GAGTCCTGGG GGTGTCTGTC AGACCAGCAG ACCTCACTTT AGTTTGTGTC
10601  TCCCTCCTGG TTCCCACCCT ACCAGACTCC AGGGAAAGCT CTTCCCACTG
10651  AGAAATAGGA AGGAAGAGAT CAAGGGCTAG GAGCAGTGAG TGACTTTTTT
10701  TAAAATGGAC ACATCCAACA TTCCCCTGCC GCCCGCACAG ACCTGGAGGG
10751  ATGTGGAGGG TGGAAGGGGG TCCCATAGAG TAAAATGAGG TGACATCAGG
10801  GCCACTACGC AGGGGCCAG TGACAGCCAA GCCCCTGTA CCTCACCTAG
10851  GGTAAGGAGA AGACACCTTC TGCCTAGAGG TGTGGACACT GGCTGAGTGC
10901  CTGGAGCCCC TGGTCACTTC CCAGTGCCCC CAGGCTGCCC GTCACACAGC
10951  ACTCCAGGCA GGGCCAGCTG TCTCCATCCT GGCTTCCTTG AAGAGCTGGC
11001  ACCAGGCCCA GCCCTGTCTC CAGAATCTGG GGAACAAACT GAGCTGTCTC
11051  CCAGAGCAAA TATGGCTCTT ACACCCAACA TACTCCTGAC ACACACACCC
11101  CAGCCCCTGA GAACAGCCAG GGTTCCTTCC TGCCCCCGCC GTCCTGCCCC
11151  CTTCCATCCT CTTGTTGGGG CTGATTTTCC TGTATTGGGC ATGGGGCACT
11201  GGTCTTCTTT GCATAAACAA GAGCCCTGGG CTGGGGGAGG GGCAGTCTTG
11251  AGAGGTGGGG TTACCTCTGT TGTTCCCCTG GACACCCAAG TGGTCTTCCT
11301  ACTCCTCCAG CCCCTTTCCT CTGGGGTCCT GAGCTAGCTG GCTCGAAGGA
11351  AGCGGGCTGG GCTGTTTCTG TAGGGCCCAT CACCATGGCA TCAGCCAGGG
11401  AGGGGCTGGG CCCAATGGGG CGTTGGCCCC CAGGCTCCCA CAGCCTTCCC
11451  TGAAGGGAGG AAGGAGGAGC AGGGAGCGGC CCTGGGCCTG TTCCCCAGAG
11501  ACGGTCACTG GGATTAGGGT ATCGACTTTC CCCAGCTTTC CAGGTGACTG
11551  CTGGTGGCGC CTATTGAATT CCGTGCCCGC CATCCGCTCC CTGGACTGCG
11601  TGGGTGGAGG TGATGGGGCG GCCACTTAGG GCGCGGTGAA GCTCCCTGGG
11651  GGAAAGGACA GATGAAGGGA GGAAGCCTGA GGGTGGAGGA GGCCCCGGGA
11701  GAAGGGTGTG GGGCAGCTC TCCGGGCAGG GTCTTTTCTG GAAAGCCAGC
11751  CAGCATTTTG TGAAAGTGAG AGTCTCCAGC CTGTCCAGCC TGGGTCACC
11801  CCGGCCCAGC TGCGCTGCCC ATCGGCTGCA TGGCCTCATG TTCCCTCCTG
11851  TTGATTCTGG CTCTCTGCCA GTCTCCTCTC TGAGCAGATC CTGATTTTGT
11901  CTTGAACTTG GGTCTCCCAG GCTGTCGTCG TCACTGGAGG TCCCACTTTG
11951  CCCTCCGGAA CTCACTGGGG CTATGTTCCT TTTGAGTCTC CTCCTCCCAC
12001  CATGCTTCGG ACCCCTCTGT AGCTGGCTCC TCCTAAGATC CTGGGGGCCA
12051  CACACCAAGC CCAACATGCC TGGACGTCAC TCCCATTTAT CCCCTTTCCC
12101  CAGAGGCAGA ACCCAGCCCT GCCCAGCTT GGCGGTGAGG GTCCAAGAGC
12151  AATGGTGGCT GAGCTCGGCC AGGTACCCCA CACCTCCCCA TCTTCTCCTC
12201  TCAGTGCTGG GCCTGGAGAC CACAGGCCAG GCCCCACAGA TCCCCAGGGG
12251  GGCTGCCCCA AGGGACTCCC CTGCCAGCCC CAGCCTCCAC CCAGGCTGGG
12301  ATGGGCTGGC TTGATGGGCT GACTCAGCAA CTGGCACTGA CACCTCCTGG
12351  AGACAGCTGG GAGGCTCCTG CTAGGGAGGG GTGAGGAGGA ACAAGGCTGG
```

FIGURE 3D

```
12401  TCTCCCTTGA AGAGTGGGAA CCCCCCTTCC CATGTGAGGG GAGGAAGTCT
12451  CTAGGGACTT GGGAAGGAGG CTCTGCAGGT GCATCGGAGC TGTCTAAATG
12501  CTGGTGGGGT CTACCGGGGG CTTCCCATCT CCTTGTCCAG CCACCCCCTC
12551  AGGTCCTGGA GCCGCCACAG AGCCACATCT AGACAGAACA GTGGAGCAGG
12601  TCCCAGTGCA GGGGAAGGAA ACAGAGGGCA CCTGAGCCCC TCAGGCTGGG
12651  TACCCTGTTT CCCCTTGAAC TGCACGACTT GGTGCTGGCA GAGCGGAGCA
12701  AGGCTCAAAG CAGGCCCTGG AGCTTTGGCA CCATATGTCA CTAGGCGAGG
12751  GGCACTGGGC TGAAGATCAG TAAGGGAAGC CCACAGCACA GAGACCAGGG
12801  CCAGAGGATG GGCATCCCAA AGGCAGCTAG CACAGCCCTG CCCTGCCAGC
12851  CGGGGGGGGC GCCCAGTAGC CACCTGCCCC CAGTCCAGCC ATGCCCCTGC
12901  CCTGTCACCC ACACCAGGCT TCATCCCCCA GCTCAGGCTG CAGCTCCAGC
12951  TGCGAGAGGC CCTGAGCGCC CGGAAGGAAG CTGTGGTAG GTTGTGGTTT
13001  CTTCAGCTCC CAGCCTACCT CCAGCAGAGG CTGCAGCCGA TGCCCTGGAG
13051  AGAGCCCCTG TCTGCCCTCT GCTGCCTGAC TCCTGTTGGG TCCTCACCTC
13101  CCAATGGGTT GCCCCATTCT GGACTTGGAT CCTTAAGGAG CACCCTGCAG
13151  TGTGGTGGAA GGAGGACAGG TTCCAAGTCA GAGACCAGGG TTGGAGTTCT
13201  GGCTGTGTGA TGTCAGGCAG TGGGCTCCAC ATCTCTGAGC CTCAGTTTCC
13251  CCATCTCAAA AACAGCTGAC AAGCCCCAGT CAGGTTGTTA TGGGAAGGTT
13301  TTTGGGAGCG CAGGGACGGT GGAGGGAGGT TGGAGGAGGT CACTAGAGCT
13351  GCCCCCTGCC TGTCCTGAGA TTTCACCCTC CCCACTTTCT CAGGGTGTCT
13401  GGCTGAAGCA GAAAGCTGCG CCTGTCCTGG TGACGGCGAC TGGTCAGACT
13451  TGTTTCTGCT CACCTAGGCG GCCGGGGGA GGGCCTGGCT GGGAGCTTTG
13501  TGGAGGGATT AGCTCTAGGG GAGAAGAGCC TCACTTACTC CCGGAACAAG
13551  ATCCCACAGG GCTGTGGGAG TGCCGGGGGG TGAGCCTGGG GCAGGTGACA
13601  GCCGAACTAG CTGGGAGTGG GCCCTGCAGT GAGGCAGGGG GTGGGCCAGG
13651  GAGAACAAGG CAAGAGGAGC TTCATTCAGG GTTCCTGAGC CTTTGTGAGC
13701  CACTCACGTT TTTACCACTC ACTTAACCGT CTTTGTTGTT GGGGTGAGGG
13751  GTCCTCGAGC CTGGATTTGG GTATGAAAAC CCAGGCAAGA AAGACCTGCC
13801  CAAGCCTTTA AAGGAATGCA AAGTCATCCT CTAGCCACCC CCAGAGATCG
13851  AAAGGCTGGG GATTGAGTCT CCTGCAGATG GTGGCGGCCT CCTGGGCTG
13901  GCAAGTTGGG ACAGAGGCCC ATAAGCCCTC CTGGGCGCGC CTTCCCACCC
13951  CTCTCGGCCC TCTCCACTCC CAGCTGGGGA TTTGGGTTTC AGAGCAGCCT
14001  GGCACACACA CCCCCACCCC ACCAGAATCT CACTCCCAGC TTCCTATGAC
14051  TATTCATTAG TATTCACAAC AATGGGAAAG TCTGGGTGTG CACAGGGATT
14101  TTTTACAGTT AGAAAGTGTT TAAGTCAATG ACCTCACTGG GCCTCAGCAA
14151  CCCTGGGAGG CAGATGGCAG TCAGAATGAT CCATAAATGA CCTGCCCCAG
14201  GTCACACAGC TCCTAAACAG GGGAGCTGGA ACCTGGCTGG GAGCCTTGAC
14251  TATCCACTGC TCATTGTCTG ATGTGCTGAG TGATAACACA GGGCCAGCAG
14301  GCTGGACAGC AGCCAGTGGC CCTGCACCAG GCCTGGAGGA GGGGGAGAGG
14351  GACAGGGACT CAGGCGTAGT CCTTGGGCAC AGGCTTCGGC TGCCTACACC
14401  CATATTCCCT CCATCATACT GTGTGTCCAG GCCTGCAGCT TCTAAGCTGA
14451  GCTGCTTACT TTGGACCAAG CATGTTGGAA ACTGTTTTCA GCTGAGTCCA
14501  AGCACTCGAA ATCTGCGTGT GCCCTTTTAG TAGGTCACAC CCTCCAGGCC
14551  ACAGCCACAC TGGGCTCCCT TTAGCCCAGC CCTGCTTTTC CCAGTCCCCT
14601  CCCCATTCAG GCTCCTCTGT TTCTGGGGTC TCTGTGCTTC CGTTGCCACC
14651  TCTGCCCTTG GGCAGCGGTG TCGGGGGAGG AGGTCCTGGA ACGCCTGAGG
14701  ATGGCCCCGT CTTGTCCAGG TCCCCTTGCT GTGCTGAACA ATAAGTTTTT
14751  GGTTATCTGC TCCTTCTGGC TCCCTTTTGG CTGGGCCATT CGGCTTGGTG
14801  GGGGTGAGAG AGAGTTCGAG TATATGGAGG AAGGCTTTAC TGTAAACACA
14851  CTGACCAGCT TTCAGTAAAC ACCTGCCTCT TCCTCCCCTG CTGCAGAGAA
14901  CGGGGTACAA AGGGGCTGGG GGTCCTCAGT CATATGCCCC AGGTCCCCAG
14951  CCAGGCTGAC GGGTGCCACA CTCTGCCCCC TCTCCAGGAG GCCAGACTG
15001  AGCCACCAAT GGGGAGGGAT AGAGGCCCGA TCAACACAGC ATGTGATTCA
15051  CCTTAGACTG TCAGAAGGGA CAGGCATGTG AGAGCTAACC TGGTCCTACC
15101  CCTCATTTGG CAGAAGAGGA AACTGAGGCT TGGACAGAGC AGTGTTTTAT
15151  CCACATCACC TAAGCAGTTA GCTGCGGTGC TGGGTATCCA CACAAGTCTT
15201  TTGAGTCCTG GGCCAGAACC CTCTCAAATT GCTGTGTAGG GATCTAGGCA
15251  AATTTGCATC CTCCCAAACC TTCCTTGGTT GGGGAGATGG GGACAGGCAG
15301  AGGACAGGGA AGGCAGAACC TGGGGCACTG TGGAATAGCC ATGGACCCTC
15351  CCCTGTCCCT GCAGCGCGAG CTTCGGCCTC GGCTCTGTAC CATGAAGAAG
15401  GGCCCCAGTG GCTATGGCTT CAACCTGCAC AGCGACAAGT CCAAGCCAGG
15451  CCAGTTCATC CGGTCAGTGG ACCCAGACTC CCCGGCTGAG GCTTCAGGGC
```

FIGURE 3E

```
15501  TCCGGGCCCA GGATCGCATT GTGGAGGTGA TGCTTCTCGC TCTCTTCCTA
15551  TCTGACTGCC CCCACCCCCT GCAGATCAGC AGCACCTGGG GCAGCCATCA
15601  TACCATCATG GGCTTGATTA GCCCACGGGC ATAGCCAACC TGGAGCTGCT
15651  GGATGGATGG GTGGATGGGA GGGAGGGAGG GAAGGGTGGT GGATGGATAG
15701  ACGGAAGGAC AGATGGACTG ACTGATGGAC TCTTCTCTTA CCTCCACTCC
15751  CCTGGGACTC CTCCTTGCCA AGCAGATACA GTGGGCAGCC TGTGATTCAC
15801  CCATCGATCA GGGGAGATGT CTGGGCCAT CTCCAGGAGC TTCCCTGCTG
15851  CCAGGCACAC AGAGTGGGGT GGCAGTAACA AAACCCCTCT CCTGAGTTAG
15901  GCCTTTATTT ATTTAGTTTT TTTTTTTTT AAATGGAGTC TCGCTTTGTT
15951  GCCCAGGCTG GGGGAGTGCA GTGGCACAAT CCCAGCTCAC TGCAACCTCC
16001  GCCTCCTGGG TTCAAGCGAT TCTCCTGCCT CAGCCTCCTG AGTAGCTGGG
16051  ATTACAGGTG CCCACCACCA CGCCTGGCTA ATGTTTGCAT TTTTAGTAGA
16101  GACAGGATTT CACCATGTTG GCCAGGCTGG TCTCAAACTC CTGACCTCAA
16151  GTGATCTGCC CGCCTCGGCC TCCAAAGTG CTGGGATTCC AGGCGTGAGC
16201  CACCTCACCC GGCCCGAGT TAGGCTTTTA GACTCGTGCA TTCAGGGCTC
16251  TGGTGCTGTG CTCCTGGGAG AGGAAACGTG AACCAAATGC TCAGGCAGGT
16301  CCCAGAATCA CAGTCTTAGA ACCTTAGAGC TAGAGATCAG CTCTCCCAAG
16351  ACTTCTCATT TTACACGTGA GAAAACCAAG GCCCAGAGAA GGAAGTCGGA
16401  CAGCAAGTCC TTACCCAGGC TGGGCCCCAC CCCGGCCTCC CAGCTCGCTC
16451  CCATCCCATC TCTCCCAGCT GTGTTTGTTT AGTCTCGTCT GGATATTTTC
16501  GTTGGCCCTT CCCATGTATC CTGCCTCCCC AGCTGACTGT CAATGGGAGG
16551  ACCCCCAGCC TAGTTCAGGA CTCTGCAGAA ATGGCGGGGG TCAGTATCCC
16601  CAGGTTGTGA ACTGCAAACT GGCTGAGAAC CAAGGTGGTC ACCCCTGCCC
16651  CCAACCCCCC TCCACTTACC TGCCCCAGAA CCAAGGCCTG TGTCCGTAAC
16701  GCCTCCCCGA CCCTGCCCTG CAGGTGAACG GGTCTGCAT GGAGGGGAAG
16751  CAGCATGGGG ACGTGGTGTC CGCCATCAGG GCTGGCGGGG ACGAGACCAA
16801  GCTGCTGGTG GTGGACAGGG AAACTGACGA GTTCTTCAAG AAATGCAGAG
16851  TGATCCCATC TCAGGAGCAC CTGAATGGTA AGCCAGGTGG GGCCACTGGC
16901  CGTCCTGGGG CTGGAGCCCC CCAAGTCAGG GATGTGAGCC AGGGCTAAGA
16951  CTGCTGGGTC CCAGGCGAGG GGTGGGCAGC TTCCCGGCAT GGGTGCTCCC
17001  TCCTCCTCCT TCATGGGAGG CCCAGAGGTG TGGGCTGGGG GAGCGGGGGC
17051  CTAGTGTAGG GAGTGGCAGT GGGTTTCTGA GGACGGCTTG TGATGGGGTC
17101  AGCTGGCATG AGGTCGGTGA GAGAGATGGA CAGATCTTCT TATTCCCGGC
17151  CAAAGCTGCA GCCCCAAAGG AGGCCCAAGC CCCCAGTCCT GTCCCCACCA
17201  GCAGACTTTC AGGGCAGTGT CAATGTGAGG AAAGGGTTAA CTCCGGGGAG
17251  GCCTCCAGCC TTTGCTTGGT CAGATCAGAG TCCAGTGACG GGGGCCGGTG
17301  CCTCCCCCTC CCTCCTCTCA GGTTGTCTTG GAAACTCAGC CTTGCTGGCT
17351  CTAGAGAGTA GTGGGTCCCC CTTCAATCCC TGGGCCCCTG CCCTCCCCAT
17401  CCCCCACCAT CACCCTGCCA AGCCTGGCGC CTCCCCCTGC CCAGGCCCGA
17451  GCCAAACAGG GCAGGGCTGC TGCACCGGGG CAGGGAGGGG TTAAGCATGC
17501  TCTGCTCCTT GGTCTGGACT TTCTCCCTGG GAAGATGGCT CCCTGGAGCG
17551  GGCAGGGGTG CTCACTGGGC CATACTGAGG GTGGAACCTC TTGGGACTTT
17601  GCAGTGGGTG GGGCCTCCTG GAGACTCAAG GTTGTATGTG TAAAAGGAGA
17651  TTCACACAAA GGTCCTGCGA CTCCCATCGC CAGCTGCAAG GGCCCACTGG
17701  GGAGGCCCTG TCCCCTTCTG GCGCAATCCA AGGCCTGAGG CTCCTAGAAG
17751  AGGGGATGGC CCCTGGAAGT CCCTAGCTGG CTCTGGGCAT GGGAGGTGGG
17801  GTACCGCCTT ACCCTTATCT CCCAAGTTCA TGGAAACCAG GTAACTCAGA
17851  TAATCCCCTT CTCCACTGAG GGGAGACTA AGGCCCAGAG AAGCCCCAGC
17901  CTTCCTCCTA GGGATCTGAT ACGAGGAAGA CACAGCTGGA ATCTGGATTC
17951  CACTCAGCTC CTGGGATACT GTCCCTGCT TCCCCCACCC CTTCACCCTG
18001  CAGGTAATTG GCCCCCTCAG ACATTCCTCC CTCTTCTGCC TGTCTCTCGG
18051  GCTAGAGGGG CTGCAGCCTC TGGCCAAAGG ACCTGAAGAG GGAGAGGCCT
18101  GGGGACAGTC CCCTCCCCGC AGTCCCTCCA GGATGGCATC CTCACCCTTT
18151  CCATAGGGAG GAATGCCCCC CTCTCCGGCT GCCAGGGTTT CACCCTGACC
18201  ACTGTGAGCT GATGGGGAGG GGACAGTGAG TGACCCTGTG TCCCAGCAGC
18251  CTGTCCTTGC CCGGGGAAGG CTGTGGGTGT CAAAAGGGAG GAGAAGATGA
18301  GAGTCAGGTA TCTCTGGCTG TGTCCTGGAC TGGGACAGG GAAAAGATAA
18351  CCAGGAATTT TAAGCTAAGA GTTCAGAAGA AGCCCTACAC TGACCAGTCC
18401  CTGGAGATGG AACAGCCACC CCTGAAGCCA TGTGGGACCC CTACCCTGAG
18451  TGAGCCCAGT GAAGGTGACC CCAGACCTGT CTTCTCTCCC TCTGACCCCT
18501  CCAGGTTTCC CACTGGCTGG GGGAGGGGAT ACCCAGGACA CACCCCTTGA
18551  GCCTTCTCGT CCCCCCTCAT TTCCTGATTG GCAAATAGGA GTTGGGATTA
```

FIGURE 3F

```
18601  TTTTCTCTTT  TTTTCTTTTT  CTTTTTCTTT  TTTTGAGAT   GGAGTCCTGC
18651  TCTGTCACCC  AGGCTGGAGT  GCAGTGGTGC  GATCTCGGCT  CACAGCAACA
18701  TCTGCCCCTA  GATTCAAGTG  ATTCTTCTGC  CTCAGTCTCC  TGAGTAGCCG
18751  GGACTACAGC  CATGCGCCAC  CACGCCCAGC  AAATTTTTAT  ATTTTTAGTA
18801  GAGATGGGGT  TTCACTATGT  TGGCCAGGAT  GGTCTCGATC  TCTTGACCTT
18851  GTGATCCGCC  CACCTCGGCC  TCCCAAAGTA  CTGCGATTAC  AAGTGTGAGC
18901  CACCGCGCCT  GGCCTTTTTT  TTTTTTTTTC  CGGACACAGT  CTCTGTCACC
18951  CAGGCTAGAG  TGCAATGGCA  CAATCTTGGC  TCACTGCAAC  CTCCACCTCC
19001  TGGGTTCAAG  CAATTCTCCT  GCCTCAGCCT  CCTGAGTAGC  TGGGATTACA
19051  GGCGCCTGCC  ACCATGCCCG  GCTAATTTTT  GTATTTTTAG  TAGGGATAGG
19101  GTTTCGCCAT  GTTGGCCAGG  CTGGTCTTGA  ACTCCTGACC  TCAGGTGATC
19151  CGCCTGCCAC  AGTCTCCCAA  AGTGCTGGGG  TCCCAGTCAT  GAGCCACCGA
19201  GCCCAGACTA  TTTTCTCTTT  CAGTTGAGGC  AGGTACTAAC  TATAGTCTGG
19251  GGTGTGGTTC  CAATTTTGGT  GTCATCATCA  TCACCTGGGA  AGCGTTTGGA
19301  AAATGTTGAT  TCTTAGGCCT  GCCCACTAAA  CCAGAATCTG  TGCTGCCAAG
19351  GTCCAGGAAT  CTGTACTTTA  ACAAGCTTCC  CACGTAGGAG  TTCCCAGGTA
19401  GGAATTCCCA  GGTAGGAATT  AGGCAGCCAT  CCTCGAATTT  CATCCCCATC
19451  TGAGACAATA  CATTTTTTAA  ACACCTTGTG  ACCCATCAGT  GCCTCATAAG
19501  ATCAATTTAG  TAGATAGAGA  CCAGCAGGTT  TTTTGGTTTG  TTTTTTTTGT
19551  TTTGTTTTGT  TTTGTTTGT   TTTGCCAGAG  TCTTGCTGTG  TTGCCCAGGC
19601  TGGAGTGTAG  TGGCGTGATC  TCGGCTCACT  GCAACCTCCA  CCTTCTGGGT
19651  TCAAACAATT  TTCCCACCTC  AGCCTCCCAA  GTAGCTAGGA  TTACAGGCGT
19701  GTGCCACCAT  GCCCAGCTAA  TTTTCTTTTT  GTCTTTTTTA  GTAGAGACGG
19751  GGTTTCACCA  TGTTGGCCAG  GCTGGTCTCA  AACTCCTAAC  CTCAAGTGAT
19801  CCAGGTGCCC  TCGGCCTCCC  AAAGTGCTGG  GATTACTGGT  GTGAGCCACT
19851  ATGCCTGGCC  CAGACATTTT  TTTGTTTTTT  TTAATGAATG  AAATTAAAAA
19901  TATCAAAGAA  CACTGTAGTA  AGGGTGTTGC  TTTGTGAAAC  TTTTATCACA
19951  CAAAATCTTT  GTGTGTGCTG  AGTCATCAAA  ATGGCAAACG  TAGGCCAGAC
20001  ATTTGCTCAC  ACCTGTAATC  CCAACACTTT  GGGAGGCCAA  GGTGGAAGGA
20051  TTGCTTGGGG  CTAGGAGTTT  GAGACCATCC  TGCATGACAT  GGCAAGGCCC
20101  CATCTCTATA  AAAAAAAAAT  TTTTTTTAAA  TAAATAAGGC  AAATGTATTC
20151  ATGGTGGGTG  GTAGTCAAAA  AAGTTTGAGA  TGTTGACCCA  GGGAACAAGA
20201  TCTAATAATC  TGCCCAAACC  CAACTCCTAC  CTCCTCTCCA  CGCTCTATTC
20251  CATCCCCGTT  CTGGACTCAC  CTCTGCTCTG  TCCTTTGCCT  AGGTCCCCTG
20301  CCTGTGCCCT  TCACCAATGG  GGAGATACAG  AAGGTAAGGG  CGGGTCCCCT
20351  GTCTCTTTGG  ATTTCAATCC  TTGGGGTGCA  TGAGACAGAT  CAGAAGGTGC
20401  TGTGGTTGGT  AGGATAGCCA  TCTGACTAAG  GCCAAAACCC  CAGGGTCCCC
20451  AGTTCCAGCT  CCTTCTTCAG  CTCCAAGCTA  TAGAACTGCC  AGAACCCTCT
20501  TGGCCTCTGC  CTGGGGCCAA  AGCTGTCAGG  AGGGAGCGGG  CTGGCTGGGC
20551  CCCTCTGCAG  CCCGCCATCC  TGGGTGACAA  GCCCCGCCT   CCAACTCCCC
20601  ACCATACAGA  AGGGGCCATT  CTTCCCCCCA  AGAACAGAGC  TTCAGTGTCT
20651  GGCCACGGGC  AGCCGGGCCC  CTGCTACTTC  TAGTCTGGGT  TGGAAGAACA
20701  AAGCCCCTCC  TCCCCCCTTC  CCTGGGCAGA  AGGGAAAGGG  GGTGAGGCCC
20751  GGGGAAGAGA  TGGTGGGGCT  GGGCGCCAGC  TGAAGCCATG  GAGGAACCCA
20801  GGAAGGGGCT  GGGTGCCAAG  CTGACGCCCC  AGCCAAAGCC  TTCGCTCTGG
20851  GACAGGCCGA  CTCAGTCAGG  CCACAGAGCA  GGAACTCTGC  AGGGTCTGCT
20901  TAAAGGTTCC  CCTTCCCTAG  GAGCTCCTGC  CAGGGTACTT  GGCAAGGGGG
20951  AGGGCCCTTG  GACCCAGCCC  TCAACCTTCT  TTCACCTCAT  CTTTGGATCT
21001  AGAACTTTCC  ATCCACCTTC  TTCTTTCAAG  GCCCTCCTTT  GCTGCTTCAG
21051  GGTTAGGGTT  TCAGGATTCC  TGGGGTCAAA  TCCTGGCAAA  CAGTCAGGTG
21101  GACCACATGA  GATTCAGGGA  GCACCACATG  GGCTCCCCAT  GCCCCCATGT
21151  GTCCCCACAT  TCCAAGAAGC  CCTCCCTGG   TCACTGGCCC  AAAAGGCAAG
21201  CCAGTACCTA  AAAGCCACAT  TGGAGTGGCC  CAGGGAGAGG  GAGCGGTTCA
21251  GCTAATCCCA  TGATGGTCTG  TTCCCATCCC  ATCCCTCCAG  CCTGAGCAGT
21301  AGAACCAGCC  TGCCCTCTGA  TCCCCAAAGG  AATGTAAAAA  GGAGCCCCAG
21351  CAGGCTCAGG  AGGTGGGAAC  CAGGGGTGGG  TGGCCAGGGC  ATCAGTGCTA
21401  CCTCTTCTCA  GTCTGAGGCC  CCTACTTCCC  CAGGAGCTCC  CTCCCTCCTC
21451  AGGACCCCCT  CACCCCATCC  TCTGACAACC  CACAACCCTC  TCCTCTCTGC
21501  CAGGAGAACA  GTCGTGAAGC  CCTGGCAGAG  GCAGCCTTGG  AGAGCCCCAG
21551  GCCAGCCCTG  GTGAGATCCG  CCTCCAGTGA  CACCAGCGAG  GAGGTAGGCC
21601  AGCCATGCGG  GGGGTGGCAA  CTGGGTTACA  GGAAGCCGAT  TCCCAGGCCC
21651  CACTTGTTCC  TGGCACACCA  GCCTGCCTTT  GAGGTCACAT  GCTGAGCCGC
```

FIGURE 3G

```
21701 ATTCTGTTCT TGTGACCTGG CTTCCCTGGG CACGGCCCCA ACGGAGCCAC
21751 CTCACCAAGG CTGAGGACCA GGGAGCCTAA TGAGGGACTG ACTCCCAACT
21801 TCCTGCCCCC ACTTCTCTTT ACAGCTGAAT TCCCAAGACA GCCCCCCAAA
21851 ACAGGACTCC ACAGCGCCCT CGTCTACCTC CTCCTCCGAC CCCATCCTAG
21901 ACTTCAACAT CTCCCTGGCC ATGGCCAAAG AGAGGGCCCA CCAGAAACGC
21951 AGCAGCAAAC GGGCCCCGCA GATGGACTGG AGCAAGAAAA ACGAACTCTT
22001 CAGCAACCTC TGAGCGCCCT GCTGCCACCC AGTGACTGGC AGGGCCGAGC
22051 CAGCATTCCA CCCCACCTTT TTCCTTCTCC CCAATTACTC CCCTGAATCA
22101 ATGTACAAAT CAGCACCCAC ATCCCCTTTC TTGACAAATG ATTTTTCTAG
22151 AGAACTATGT TCTTCCCTGA CTTAGGGAA GGTGAATGTG TTCCCGTCCT
22201 CCCGCAGTCA GAAAGGAGAC TCTGCCTCCC TCCTCCTCAC TGAGTGCCTC
22251 ATCCTACCGG GTGTCCCTTT GCCACCCTGC CTGGGACATC GCTGGAACCT
22301 GCACCATGCC AGGATCATGG GACCAGGCGA GAGGGCACCC TCCCTTCCTC
22351 CCCCATGTGA TAAATGGGTC CAGGGCTGAT CAAAGAACTC TGACTGCAGA
22401 ACTGCCGCTC TCAGTGGACA GGGCATCTGT TACCCTGAGA CCTGTGGCAG
22451 ACACGTCTTG TTTTCATTTG ATTTTTGTTA AGAGTGCAGT ATTGCAGAGT
22501 CTAGAGGAAT TTTTGTTTCC TTGATTAACA TGATTTTCCT GGTTGTTACA
22551 TCCAGGGCAT GGCAGTGGCC TCAGCCTTAA ACTTTTGTTC CTACTCCCAC
22601 CCTCAGCGAA CTGGGCAGCA CGGGGAGGGT TTGGCTACCC CTGCCCATCC
22651 CTGAGCCAGG TACCACCATT GTAAGGAAAC ACTTTCAGAA ATTCAGCTGG
22701 TTCCTCCAAA CCCTTCAGCC TCCGTGTGTT CCTTGGAAGT TTTGTCCTCT
22751 GGCCTTGGAC CCCTTATAGG TAGAAATTGA GAAATGGTAA GCCAAGGTGG
22801 TCTTTGGCTG GGAGGGTGGG GTACACTGGA GGGAGGGCCA TCAAGGGCTC
22851 CCTGTGACCC CAAGCCTGGG TAGCTTTAGC TAGAGGGCCT AGCTGCAGTC
22901 CTGTAGGAAG GAAGATGCAT GCACCCAGCC GGGTATTCAG CTTGGTGTGG
22951 TCAGTGTGCC TGTGTGCTGG GCTGCAAGCA CCGATTGTGG GCTGGGGACC
23001 CCTTGTCTAA CGGGGATATT TACAAGGGGA AGTGGGAGCT CAGACCAACG
23051 TTCTCAGAGG ACTCTGGGAG GTTCCTTTAA TTCCAGAAGC GTGGAAAGTG
23101 TGTCCCAGGA TGGAGCTGGG TTTGGAATGT GAGGACTTGG CTTTACTCTT
23151 TCTGCCTATA GCCAGTGGGG TGCAGAATTC CAGGGGCAG GCTGGGCTGG
23201 TGCCAGATCC TCTATCTTAT CTGGCCATTG TGACCTGATT GGAGGGCAAG
23251 TGTCCAGTGC CAGGGGAAAA CAAACCGGTC CACTGAGCCC GGGGACATGC
23301 TGTGTGGCTA GCTGGGGTGG AAGGGACTGT TCAAGGGCAA GGTGCCCTGC
23351 CCCCAACAAA AGACCCAGGT CCCTGATACC TTTGGCACCT GAAGCCTGAT
23401 CTGGAGGTCC AGGAAGGTGG CTTGCAAGAG CTAGGCTGCA GAGCCGGGAG
23451 GTTCCGGGCA GGTGCTCAGG AGGAAGGTGC CCCCAGGCTA GTCTCCACCC
23501 AACCCAAAGG GACACCTCTC AGAAAATAGG CTCCTGGGCT GAGGGGAATG
23551 AGTAAAGCAG GTAGATCTGG AATCAGGGAG TGGACAGTGT CCCCCAGGCC
23601 AGTCACTATC TGGCCATCTC CTGCTCCTTG TCAGAGGAAC CATCCAAAAC
23651 CCTTACCACA GCAGTGCCCT GCTCAGCTGA CCTGCCCCCA CCCCACCCTT
23701 GCTTCTACCC TTTGGCCCCT GACAGATTCC CCTCCACAGG GGTCGTGGAG
23751 GGCCCCTCCC TATCTCACCT GCTGGGTGGG GAAGCCCTGG GGGACCTTTG
23801 ACTCTTCATT AACCTGAAGA CTGGTGGAAG GAATGGGTGG CCCCAAGGGA
23851 ACTCTCATTG CTGAGGTACA CATGGTACGA AGGGAGCCAC GGCAAGCAAC
23901 GCGTTCGTTT TATAATGTTT GTTTTATACT GAGGCATGTT TTCGGTTCCA
23951 GTTGTTCACA TGCAGTCTGC TGTGAGACTC CAAGATCAAG GGTGCTGGGA
24001 GGCCTTAGGC AAGTCACCTT ACTTATCTAA GACTGTTTCC CCACCTGGAA
24051 GATGCCCTAC AAGCCTCCTG TGGCTGTGTT TAGAAAGCAT GCCCGGCCTT
24101 TCTTGACAGC CAGCCACCCC AGATGATGGC AGGGCAAGGA AGACTGTTAG
24151 GAGTCAGAGT GCTCCCCTCA GGTGGAAGGA AACTGGGCCA ACTCTACTTT
24201 GTAAGCCATA GGGTGCCAGG TAGCCCGGCC ACCCTGAGCC TGTGCCTCCA
24251 CTGCCCCCGC GTGGCCAGTC AGGTGCAGCT GCTCCCAGAG ATGGAGGGTG
24301 AGGAACAGAC GTGGGAGCAC CAGAGGGACA GAGCTGATGG CCTGACGCTC
24351 TCTTCAGGAG GGCACCCCCA AGGGGCCTCT GCTTCCTCAG TGCCCCCTGA
24401 GCTTTATCAG CAGAGGGGTG TTTTCCAGCC ACAAGGAGCT GTATCTAACA
24451 CTAATGCCTT TAAACTCAAG ACTGGCTCCA GGAGAGAGGA GGACGGACAC
24501 TAGGTTGAGG GGCCAGGCCA CACTCACTCT GGACCACCTG TTGTTCCCGG
24551 GTCAAGTTCC CAGGGTCACA CCAGCCTGCC TCTGCAGGAC AAGAGGACCA
24601 AGCTGCCCTT GAGTGGACAC TGTGAGGCTG GGCTTGTGG TAGCTCTTCA
24651 CACGGACCAA ACGGGAAAAT CAGGAAAGCT GGTAGTGCCT GGAGCTTCAC
24701 TCCCAGC  (SEQ ID NO:3)
```

FIGURE 3H

FEATURES:

| | |
|---|---|
| Start: | 2196 |
| Exon: | 2196-2636 |
| Intron: | 2637-15364 |
| Exon: | 15365-15526 |
| Intron: | 15527-16723 |
| Exon: | 16724-16877 |
| Intron: | 16878-20292 |
| Exon: | 20293-20333 |
| Intron: | 20334-21503 |
| Exon: | 21504-21593 |
| Intron: | 21594-21824 |
| Exon: | 21825-22010 |
| Stop: | 22011 |

CHROMOSOME MAP POSITION:
Chromosome 17

ALLELIC VARIANTS (SNPs):

| DNA Position | Major | Minor |
|---|---|---|
| 329 | T | C |
| 411 | A | G |
| 2014 | G | C T |
| 2650 | G | A |
| 5747 | A | G |
| 7980 | A | G |
| 8876 | C | T |
| 12042 | T | C |
| 12137 | G | A |
| 19971 | A | G |
| 20119 | A | T |
| 20668 | C | - |
| 20672 | - | T |
| 21016 | C | T |
| 21327 | T | C A |
| 22433 | C | T |
| 22949 | G | A |
| 24211 | G | A |

Context:

| DNA Position | |
|---|---|
| 329 | GCTCCTGGAGCTGGTGGGAGACAAGATTAAGCAAACCTCCCCTGACATGTATCCCTTTGA<br>CCCCAAGCTCTGCCTCCTCCCTGACCACCCATGCCCTTTCCTTTAACTTCTCAAACAGAT<br>ACCAGGGCCTAAACTGCTTTACCTCCCCTCCTACTGAGTCAGGTTAGGTGGTGGGAGGTC<br>ACCCATTTCCGAGTTAAACCAATGCAATATGAGTAAAACAAAGTCATGTGGGTATGTCTG<br>GGGTAGAGAGAGGGGTAGCAAGTTCATGTGTCCTCCTTGGTCACATATCTCCCAAAGCTC<br>[T,C]<br>GATCCCTGCCATGGGAAGTGGACAGGAAACATGAGGTCATGACCTGCAGGCATCTTTACT<br>GCAGCTCTGCCGGCCTGGAGGGGGAGAGGGGGAGGAAGAAGTATGCGCTGCACATTTCTG<br>AGGCTACTGCATTTGCTTTCAAGGCAGAAATCTTGCTCTGAGCAGTCAGCGGCTCCAGTT<br>TGGGCCCGATAAGGAAGTTCTCCGTGGCCTCCCTCAGGCAGAGCAGGGAGGAGGCTGACA<br>TTGCCAGTCTCTTCTGGGCCCAAGGCAGGTTGCAGGAGATCCAATCCCATAGACAGCTC |
| 411 | GACCACCCATGCCCTTTCCTTTAACTTCTCAAACAGATACCAGGGCCTAAACTGCTTTAC<br>CTCCCCTCCTACTGAGTCAGGTTAGGTGGTGGGAGGTCACCCATTTCCGAGTTAAACCAA<br>TGCAATATGAGTAAAACAAAGTCATGTGGGTATGTCTGGGGTAGAGAGAGGGGTAGCAAG<br>TTCATGTGTCCTCCTTGGTCACATATCTCCCAAAGCTCTGATCCCTGCCATGGGAAGTGG<br>ACAGGAAACATGAGGTCATGACCTGCAGGCATCTTTACTGCAGCTCTGCCGGCCTGGAGG |

FIGURE 3I

[A,G]
GGAGAGGGGGAGGAAGAAGTATGCGCTGCACATTTCTGAGGCTACTGCATTTGCTTTCAA
GGCAGAAATCTTGCTCTGAGCAGTCAGCGGCTCCAGTTTGGGCCCGATAAGGAAGTTCTC
CGTGGCCTCCCTCAGGCAGAGCAGGGAGGAGGCTGACATTGCCAGTCTCTTCTGGGGCCC
AAGGCAGGTTGCAGGAGATCCAATCCCATAGACAGCTCTGGGCCTCTTGCATTTGAGTTT
TTCAGAATTAAACTGCAGTATTTTGGAAAGCACATCCTGTCCACTGTTTCTTTGAAGTGA

2014    CCGGGAATTCGGCGAGCCCCGCCCCTGCCACCCCAGCGCCGGCCGCTCGGTAACAAACAC
TTCCACTTCCTGAGCGCTAGTCTTCGCCCGCCGCGGGGCGCCGCGCCGAGCGCAGGCCCC
GCCCCGCGCGTTCCCAATGGCCGGCGCCGTTCACCCGGCCGGAGCGCCCAGGCCTGCAGC
CCCCTATTGGCCCGCGGGAGGTCCCCACCCTCAGCGCGGCCCCGCCCCCGGGGTAAGGAG
CCGGGGCGGACTCTGGGACGCTCAGACGCCGCGCGGGGCGGGGATTGGTCTGTGCTCCTC
[G,C,T]
CTCGGCTCCTCGCGGCTCGCGGCGGCCGACGGTTCCTGGGACACCTGCTTGCTTGGCCCG
TCCGGCGGCTCAGGGCTTCTCTGCTGCGCTCCCGGTTCGCTGGACGGGAAGAAGGGCTGG
GCCGTCCCGTCCCGTCCCCATCGGAACCCCAAGTCGCGCCGCTGACCCGTCGCAGGGCGA
GATGAGCGCGGACGCAGCGGCCGGGGCGCCCTGCCCCGGCTCTGCTGCCTGGAGAAGGG
TCCGAACGGCTACGGCTTCCACCTGCACGGGGAGAAGGGCAAGTTGGGCCAGTACATCCG

2650    GGCTGCTGGCGGGGGACCGGCTGGTGGAGGTGAACGGCGAAAACGTGGAGAAGGAGACCC
ACCAGCAGGTGGTGAGCCGCATCCGCGCCGCACTCAACGCCGTGCGCCTGCTGGTGGTCG
ACCCCGAGACGGACGAGCAGCTGCAGAAGCTCGGCGTCCAGGTCCGAGAGGAGCTGCTGC
GCGCCCAGGAAGCGCCGGGGCAGGCCGAGCCGCCGGCCGCCGCCGAGGTGCAGGGGCTG
GCAACGAAAATGAGCCTCGCGAGGCCGACAAGAGCCACCCGGAGCAGGTAAGCGGGGCCC
[G,A]
AGCCGCGCAGGCTGGCATGGAGTGGGAGGAGGATCCGGAGAGACCCAGGTGCCCCGGCCG
TCCAGCCCCGCGCCCGCCGTCGTTTTTCTGAAACTCGAGCTGCGAGGGGGAGACCGCTTC
CGCCCGCCGACCAGGCGCCCTGACACATCCTAGGCAGGCCTGGGGCTGCGTCCCGCGACC
TCCTCTCCTTCCCAGGCTGTGCTGGGAGCTTGAGCGCCTTTGCCGCCTGCACCTCTTGTT
CCCTGGCCTTTGGGAGGGCGGCGCAGGGGAACCCAGCCCCCTTCCCTCGGGTCTGTGGGT

5747    TGGCACACAGTCAGTGCCTGATCGATGGTCACTGTGGGTTAAGAATGATACGTTGTGGCC
AGGTGTGGTGGCTCACACCTGTAATCCCAGCACTTTGGGAGGCCAAAGTGGGAGGATCGC
CTGAGCCCAGGAGTTTGAGACCAGCCTAGGCAACATGACAAGACCCTGTCTCTATTAAAT
TTTTTCTTTTTTTTTTTTAAGAGTTATATGCTGTTCCATGGCCCTTCTCCATCTGGCAGC
CTGTTCTCACCACTGCCTCCCTACCCCCAAAACCACACCCAGGGTCCGAATTCCCCTCTA
[A,G]
CCTCTAAGCCTTCACACCCTGACACTTCTGTCCCCTCCCAGGGAGCCTGTCCTTAATCCA
GTAGGCAGAGTTAGCATTTCCTTTCCTTCACTTTTTTTGTTTTTGTTTTGTTTTGTTT
TTTTTGAGACAGATTCCACCCAGGCTGGAGTGGTGTCGCAACCTCGCCTCGCTGCAGCCT
CGACCTCCAGGGCTCAATCGATCCTCCCACCTCATTCTCCCTAGTAGCTGGGACTACAGG
CATGCACCACTATTCCCAGCTAATTTTTAAATTCTTTGTAGAGATGGAGTTTCACCGTGT

7980    CCTTTAGGCACTCTACCTATGACATAAAGATGTTGACATGCATTTCTTTCTTTCTTTCTT
TCTTTCTTTCTTTTTTTTTTTTTTTTTTTTCCTGAGACAGTCTTGCTCTGTTGCCCAG
GCTGGAGTGCAGTGGTGTGATCTCGGCTCACTGCAACCTCCGTCTCTCAAGTTCAAGCAA
TTGTCCTGCCTCAGCCTTCCATGTAGCTAGGATTACAAACACCCGCCACCACACCCTGCT
AATTTTTGTATTTTTAGTAGAGACGGAGTTTCACCACGGTGGCCAGGCTGGGTGGCACCT
[A,G]
TCACAACACCCTGCTAATTTTTGTATTTTTAGTAGAGATGGGGTTTCACCACATTGGCCA
GGCTGGTTTCAAACTCCTGACCTCAGGTAATCCACCTGCCTCGGTCTCCCAAAGTGCTGG
GATTATAGGCATGAGCCACCACACCCAGCCAATATGCATTTCATTGTCCCCAGACAAAT
TAGCTATTGTTTTCTCTATTTTGTAGGTTGACAGTAAGTGTTCAATACATGATAGCTACT
ATTTGTGTCTAGCACTGTGCTAAGTACTAACCTTGCCTGTCTCATTTAATCCACATGACC

8876    TCCAGGGCTTCCAGGTGCTCCTGTCCCTAGCAGGGCATCCTTGCAGTGCCTCAGCCCATA
AGTGGCAGGCTCCTGTCCCCATCCCTTCTCACGTGATGTGATAGGTCAATCTGGAATCTG
GTAACCAAGTATCTACCCCCGCCCTCACTCCCCAGAACCTGCACAGAGAGCCCCCCTCAA
GGGTGGTCTTCACTGTTGACCGAAGCCTTCCCCTCATGGTAGGACAACTCACCATGTCCC
CAGACTCCTAGGCAATGTTTAGGTCCCTAGGCCCTAGAAAAGGACAAGAGTTACAGATTC
[C,T]
CTGAGGTCCAGGTCACCTCGGGGTGGTGTGGGAACACACAGAGAATGCTGGCCAGGTTCA

FIGURE 3J

```
           AGTCCCACTCACTGCTGGGTGCTGAGAGCTCTGAATTCTCCGAGACAGGCTGCAGCCTCT
           CCCTGTGCTAAGGTCAGGGGAACAGCAATGGCCAGGGGTATTTAGAGGAGTGTGTTTGGG
           GCAGTCTCAGGCAGCACAGGTCTGTGCTGTCCGGGCAGCAGCCACCAGCTTCGCGAGGCT
           CCCGGGCACTCGAGATGTGCTGGTCCACATGCAGACGTGCTGTGTGTGCAAAATGCACAC

12042      AAAGCCAGCCAGCATTTTGTGAAAGTGAGAGTCTCCAGCCTGTCCAGCCCTGGGTCACCC
           CGGCCCAGCTGCGCTGCCCATCGGCTGCATGGCCTCATGTTCCCTCCTGTTGATTCTGGC
           TCTCTGCCAGTCTCCTCTCTGAGCAGATCCTGATTTTGTCTTGAACTTGGGTCTCCCAGG
           CTGTCGTCGTCACTGGAGGTCCCACTTTGCCCTCCGGAACTCACTGGGGCTATGTTCCTT
           TTGAGTCTCCTCCTCCCACCATGCTTCGGACCCCTCTGTAGCTGGCTCCTCCTAAGATCC
           [T,C]
           GGGGGCCACACACCAAGCCCAACATGCCTGGACGTCACTCCCATTTATCCCCTTTCCCCA
           GAGGCAGAACCCAGCCCTGCCCCAGCTTGGCGGTGAGGGTCCAAGAGCAATGGTGGCTGA
           GCTCGGCCAGGTACCCCACACCTCCCCATCTTCTCCTCTCAGTGCTGGGCCTGGAGACCA
           CAGGCCAGGCCCCACAGATCCCCAGGGGGCTGCCCCAAGGGACTCCCCTGCCAGCCCCA
           GCCTCCACCCAGGCTGGGATGGGCTGGCTTGATGGGCTGACTCAGCAACTGGCACTGACA

12137      CATGTTCCCTCCTGTTGATTCTGGCTCTCTGCCAGTCTCCTCTCTGAGCAGATCCTGATT
           TTGTCTTGAACTTGGGTCTCCCAGGCTGTCGTCGTCACTGGAGGTCCCACTTTGCCCTCC
           GGAACTCACTGGGGCTATGTTCCTTTTGAGTCTCCTCCTCCCACCATGCTTCGGACCCCT
           CTGTAGCTGGCTCCTCCTAAGATCCTGGGGGCCACACACCAAGCCCAACATGCCTGGACG
           TCACTCCCATTTATCCCCTTTCCCCAGAGGCAGAACCCAGCCCTGCCCCAGCTTGGCGGT
           [G,A]
           AGGGTCCAAGAGCAATGGTGGCTGAGCTCGGCCAGGTACCCCACACCTCCCCATCTTCTC
           CTCTCAGTGCTGGGCCTGGAGACCACAGGCCAGGCCCCACAGATCCCCAGGGGGCTGCC
           CCAAGGGACTCCCCTGCCAGCCCCAGCCTCCACCCAGGCTGGGATGGGCTGGCTTGATGG
           GCTGACTCAGCAACTGGCACTGACACCTCCTGGAGACAGCTGGGAGGCTCCTGCTAGGGA
           GGGGTGAGGAGGAACAAGGCTGGTCTCCCTTGAAGAGTGGGAACCCCCCTTCCCATGTGA

19971      AGCCTCCCAAGTAGCTAGGATTACAGGCGTGTGCCACCATGCCCAGCTAATTTTCTTTTT
           GTCTTTTTTAGTAGAGACGGGGTTTCACCATGTTGGCCAGGCTGGTCTCAAACTCCTAAC
           CTCAAGTGATCCAGGTGCCCTCGGCCTCCCAAAGTGCTGGGATTACTGGTGTGAGCCACT
           ATGCCTGGCCCAGACATTTTTTGTTTTTTTTAATGAATGAAATTAAAAATATCAAAGAA
           CACTGTAGTAAGGGTGTTGCTTTGTGAAACTTTTATCACACAAAATCTTTGTGTGTGCTG
           [A,G]
           GTCATCAAAATGGCAAACGTAGGCCAGACATTTGCTCACACCTGTAATCCCAACACTTTG
           GGAGGCCAAGGTGGAAGGATTGCTTGGGGCTAGGAGTTTGAGACCATCCTGCATGACATG
           GCAAGGCCCCATCTCTATAAAAAAAAAATTTTTTTTAAATAAATAAGGCAAATGTATTCA
           TGGTGGGTGGTAGTCAAAAAAGTTTGAGATGTTGACCCAGGGAACAAGATCTAATAATCT
           GCCCAAACCCAACTCCTACCTCCTCTCCACGCTCTATTCCATCCCCGTTCTGGACTCACC

20119      CCAAAGTGCTGGGATTACTGGTGTGAGCCACTATGCCTGGCCCAGACATTTTTTGTTTT
           TTTTAATGAATGAAATTAAAAATATCAAAGAACACTGTAGTAAGGGTGTTGCTTTGTGAA
           ACTTTTATCACACAAAATCTTTGTGTGTGCTGAGTCATCAAAATGGCAAACGTAGGCCAG
           ACATTTGCTCACACCTGTAATCCCAACACTTTGGGAGGCCAAGGTGGAAGGATTGCTTGG
           GGCTAGGAGTTTGAGACCATCCTGCATGACATGGCAAGGCCCCATCTCTATAAAAAAAAA
           [A,T]
           TTTTTTTAAATAAATAAGGCAAATGTATTCATGGTGGGTGGTAGTCAAAAAAGTTTGAG
           ATGTTGACCCAGGGAACAAGATCTAATAATCTGCCCAAACCCAACTCCTACCTCCTCTCC
           ACGCTCTATTCCATCCCCGTTCTGGACTCACCTCTGCTCTGTCCTTTGCCTAGGTCCCCT
           GCCTGTGCCCTTCACCAATGGGGAGATACAGAAGGTAAGGGCGGGTCCCCTGTCTCTTTG
           GATTTCAATCCTTGGGGTGCATGAGACAGATCAGAAGGTGCTGTGGTTGGTAGGATAGCC

20668      TCCTTGGGGTGCATGAGACAGATCAGAAGGTGCTGTGGTTGGTAGGATAGCCATCTGACT
           AAGGCCAAAACCCCAGGGTCCCCAGTTCCAGCTCCTTCTTCAGCTCCAAGCTATAGAACT
           GCCAGAACCCTCTTGGCCTCTGCCTGGGGCCAAAGCTGTCAGGAGGGAGCGGGCTGGCTG
           GGCCCCTCTGCAGCCCGCCATCCTGGGTGACAAGCCCCGCCTCCAACTCCCCACCATAC
           AGAAGGGGCCATTCTTCCCCCCAAGAACAGAGCTTCAGTGTCTGGCCACGGGCAGCCGGG
           [C,-]
           CCCTGCTACTTCTAGTCTGGGTTGGAAGAACAAAGCCCCTCCTCCCCCCTTCCCTGGGCA
           GAAGGGAAAGGGGGTGAGGCCCGGGGAAGAGATGGTGGGGCTGGGCGCCAGCTGAAGCCA
           TGGAGGAACCCAGGAAGGGGCTGGGTGCCAAGCTGACGCCCCAGCCAAAGCCTTCGCTCT
```

FIGURE 3K

```
        GGGACAGGCCGACTCAGTCAGGCCACAGAGCAGGAACTCTGCAGGGTCTGCTTAAAGGTT
        CCCCTTCCCTAGGAGCTCCTGCCAGGGTACTTGGCAAGGGGGAGGGCCCTTGGACCCAGC

20672   TGGGGTGCATGAGACAGATCAGAAGGTGCTGTGGTTGGTAGGATAGCCATCTGACTAAGG
        CCAAAACCCCAGGGTCCCCAGTTCCAGCTCCTTCTTCAGCTCCAAGCTATAGAACTGCCA
        GAACCCTCTTGGCCTCTGCCTGGGGCCAAAGCTGTCAGGAGGGAGCGGGCTGGCTGGGCC
        CCTCTGCAGCCCGCCATCCTGGGTGACAAGCCCCCGCCTCCAACTCCCCACCATACAGAA
        GGGGCCATTCTTCCCCCCAAGAACAGAGCTTCAGTGTCTGGCCACGGGCAGCCGGGCCCC
        [-,T]
        GCTACTTCTAGTCTGGGTTGGAAGAACAAAGCCCCTCCTCCCCCCTTCCCTGGGCAGAAG
        GGAAAGGGGGTGAGGCCCGGGGAAGAGATGGTGGGGCTGGCGCCAGCTGAAGCCATGGA
        GGAACCCAGGAAGGGGCTGGGTGCCAAGCTGACGCCCCAGCCAAAGCCTTCGCTCTGGGA
        CAGGCCGACTCAGTCAGGCCACAGAGCAGGAACTCTGCAGGGTCTGCTTAAAGGTTCCCC
        TTCCCTAGGAGCTCCTGCCAGGGTACTTGGCAAGGGGGAGGGCCCTTGGACCCAGCCCTC

21016   CCTTCCCTGGGCAGAAGGGAAAGGGGGTGAGGCCCGGGGAAGAGATGGTGGGGCTGGGCG
        CCAGCTGAAGCCATGGAGGAACCCAGGAAGGGGCTGGGTGCCAAGCTGACGCCCCAGCCA
        AAGCCTTCGCTCTGGGACAGGCCGACTCAGTCAGGCCACAGAGCAGGAACTCTGCAGGGT
        CTGCTTAAAGGTTCCCCTTCCCTAGGAGCTCCTGCCAGGGTACTTGGCAAGGGGGAGGGC
        CCTTGGACCCAGCCCTCAACCTTCTTTCACCTCATCTTTGGATCTAGAACTTTCCATCCA
        [C,T]
        CTTCTTCTTTCAAGGCCCTCCTTTGCTGCTTCAGGGTTAGGGTTTCAGGATTCCTGGGGT
        CAAATCCTGGCAAACAGTCAGGTGGACCACATGAGATTCAGGGAGCACCACATGGGCTCC
        CCATGCCCCCATGTGTCCCCACATTCCAAGAAGCCCCTCCCTGGTCACTGGCCCAAAAGG
        CAAGCCAGTACCTAAAAGCCACATTGGAGTGGCCCAGGGAGAGGGAGCGGTTCAGCTAAT
        CCCATGATGGTCTGTTCCCATCCCATCCCTCCAGCCTGAGCAGTAGAACCAGCCTGCCCT

21327   CAAGGCCCTCCTTTGCTGCTTCAGGGTTAGGGTTTCAGGATTCCTGGGGTCAAATCCTGG
        CAAACAGTCAGGTGGACCACATGAGATTCAGGGAGCACCACATGGGCTCCCCATGCCCCC
        ATGTGTCCCCACATTCCAAGAAGCCCCTCCCTGGTCACTGGCCCAAAAGGCAAGCCAGTA
        CCTAAAAGCCACATTGGAGTGGCCCAGGGAGAGGGAGCGGTTCAGCTAATCCCATGATGG
        TCTGTTCCCATCCCATCCCTCCAGCCTGAGCAGTAGAACCAGCCTGCCCTCTGATCCCCA
        [T,C,A]
        AGGAATGTAAAAAGGAGCCCCAGCAGGCTCAGGAGGTGGGAACCAGGGGTGGGTGGCCAG
        GGCATCAGTGCTACCTCTTCTCAGTCTGAGGCCCCTACTTCCCCAGGAGCTCCCTCCCTC
        CTCAGGACCCCCTCACCCCATCCTCTGACAACCCACAACCCTCTCCTCTCTGCCAGGAGA
        ACAGTCGTGAAGCCCTGGCAGAGGCAGCCTTGGAGAGCCCCAGGCCAGCCCTGGTGAGAT
        CCGCCTCCAGTGACACCAGCGAGGAGGTAGGCCAGCCATGCGGGGGGTGGCAACTGGGTT

22433   GACAAATGATTTTTCTAGAGAACTATGTTCTTCCCTGACTTTAGGGAAGGTGAATGTGTT
        CCCGTCCTCCCGCAGTCAGAAAGGAGACTCTGCCTCCCTCCTCCTCACTGAGTGCCTCAT
        CCTACCGGGTGTCCCTTTGCCACCCTGCCTGGGACATCGCTGGAACCTGCACCATGCCAG
        GATCATGGGACCAGGCGAGAGGGCACCCTCCCTTCCTCCCCCATGTGATAAATGGGTCCA
        GGGCTGATCAAAGAACTCTGACTGCAGAACTGCCGCTCTCAGTGGACAGGGCATCTGTTA
        [C,T]
        CCTGAGACCTGTGGCAGACACGTCTTGTTTTCATTTGATTTTTGTTAAGAGTGCAGTATT
        GCAGAGTCTAGAGGAATTTTTGTTTCCTTGATTAACATGATTTTCCTGGTTGTTACATCC
        AGGGCATGGCAGTGGCCTCAGCCTTAAACTTTTGTTCCTACTCCCACCCTCAGCGAACTG
        GGCAGCACGGGGAGGGTTTGGCTACCCCTGCCCATCCCTGAGCCAGGTACCACCATTGTA
        AGGAAACACTTTCAGAAATTCAGCTGGTTCCTCCAAACCCTTCAGCCTCCGTGTGTTCCT

22949   CCCTGAGCCAGGTACCACCATTGTAAGGAAACACTTTCAGAAATTCAGCTGGTTCCTCCA
        AACCCTTCAGCCTCCGTGTGTTCCTTGGAAGTTTTGTCCTCTGGCCTTGGACCCCTTATA
        GGTAGAAATTGAGAAATGGTAAGCCAAGGTGGTCTTTGGCTGGGAGGGTGGGTACACTG
        GAGGGAGGGCCATCAAGGGCTCCCTGTGACCCCAAGCCTGGGTAGCTTTAGCTAGAGGGC
        CTAGCTGCAGTCCTGTAGGAAGGAAGATGCATGCACCCAGCCGGGTATTCAGCTTGGTGT
        [G,A]
        GTCAGTGTGCCTGTGTGCTGGGCTGCAAGCACCGATTGTGGGCTGGGGACCCCTTGTCTA
        ACGGGGATATTTACAAGGGGAAGTGGGAGCTCAGACCAACGTTCTCAGAGGACTCTGGGA
        GGTTCCTTTAATTCCAGAAGCGTGGAAAGTGTGTCCCAGGATGGAGCTGGGTTTGGAATG
        TGAGGACTTGGCTTTACTCTTTCTGCCTATAGCCAGTGGGGTGCAGAATTCCCAGGGGCA
        GGCTGGGCTGGTGCCAGATCCTCTATCTTATCTGGCCATTGTGACCTGATTGGAGGGCAA
```

FIGURE 3L

24211    TATAATGTTTGTTTTATACTGAGGCATGTTTTCGGTTCCAGTTGTTCACATGCAGTCTGC
         TGTGAGACTCCAAGATCAAGGGTGCTGGGAGGCCTTAGGCAAGTCACCTTACTTATCTAA
         GACTGTTTCCCCACCTGGAAGATGCCCTACAAGCCTCCTGTGGCTGTGTTTAGAAAGCAT
         GCCCGGCCTTTCTTGACAGCCAGCCACCCCAGATGATGGCAGGGCAAGGAAGACTGTTAG
         GAGTCAGAGTGCTCCCCTCAGGTGGAAGGAAACTGGGCCAACTCTACTTTGTAAGCCATA
         [G,A]
         GGTGCCAGGTAGCCCGGCCACCCTGAGCCTGTGCCTCCACTGCCCCCGCGTGGCCAGTCA
         GGTGCAGCTGCTCCCAGAGATGGAGGGTGAGGAACAGACGTGGGAGCACCAGAGGGACAG
         AGCTGATGGCCTGACGCTCTCTTCAGGAGGGCACCCCCAAGGGGCCTCTGCTTCCTCAGT
         GCCCCCTGAGCTTTATCAGCAGAGGGTGTTTTCCAGCCACAAGGAGCTGTATCTAACAC
         TAATGCCTTTAAACTCAAGACTGGCTCCAGGAGAGAGGAGGACGGACACTAGGTTGAGGG

FIGURE 3M

ISOLATED HUMAN TRANSPORTER PROTEINS, NUCLEIC ACID MOLECULES ENCODING HUMAN TRANSPORTER PROTEINS AND USES THEREOF

This application is a divisional application of U.S. patent application Ser. No. 09/740,027, filed Dec. 20, 2000, now U.S. Pat. No. 6,485,939.

FIELD OF THE INVENTION

The present invention is in the field of transporter cofactor proteins that are related to the sodium/hydrogen exchanger-regulatory factor (NHE-RF) subfamily, recombinant DNA molecules, and protein production. The present invention specifically provides novel peptides and proteins that effect ligand transport and nucleic acid molecules encoding such peptide and protein molecules, all of which are useful in the development of human therapeutics and diagnostic compositions and methods.

BACKGROUND OF THE INVENTION

Transporter Regulatory Factors/Cofactors

Transporter proteins regulate many different functions of a cell, including cell proliferation, differentiation, and signaling processes, by regulating the flow of molecules such as ions and macromolecules, into and out of cells. Transporters are found in the plasma membranes of virtually every cell in eukaryotic organisms. Transporters mediate a variety of cellular functions including regulation of membrane potentials and absorption and secretion of molecules and ion across cell membranes. When present in intracellular membranes of the Golgi apparatus and endocytic vesicles, transporters, such as chloride channels, also regulate organelle pH. For a review, see Greger, R. (1988) *Annu. Rev. Physiol.* 50:111–122.

The novel human protein provided by the present invention is related to transporter regulatory factors, also referred to as transporter cofactors. In particular, the protein of the present invention is similar to regulatory factors of sodium/ hydrogen exchangers (solute carrier family 9), referred to as sodium/hydrogen exchanger-regulatory factors (NHE-RFs). NHE-RFs participate in the protein kinase A regulation of sodium/hydrogen exchangers, such as those found at the renal brush border, and are typically found in actin-rich structures (Reczek et al., *J Cell Biol* 1997 Oct. 6;139(1):169–79; Weinman et al., J Clin Invest 1995 May;95(5):2143–9). Furthermore, the protein of the present invention shows a high degree of similarity to ezrin-radixin-moesin (ERM) proteins, which are related to the NHE-RF family, particularly ERM-binding phosphoprotein 50 protein (EBP50). The ERM family of proteins are membrane-cytoskeletal linking proteins that have NH2— and COOH-terminal domains that bind the plasma membrane and the actin cytoskeleton, respectively (Reczek et al., *J Cell Biol* 1997 Oct. 6;139(1):169–79).

ERM proteins are found in high concentrations in the apical portion of polarized microvilli-containing epithelial cells, which are abundant in such locations as the placenta and intestinal brush border; the actin filaments within microvilli must attach to the epithelial cell membranes in order to properly assemble and maintain the microvilli. ERM proteins are involved in linking integral membrane proteins and cytoskeletal proteins such as actin. Actin cytoskeletal assembly requires activation of sodium/ hydrogen exchangers, which is modulated by NHE-RF proteins.

EBP50 binding interactions are involved in such important biological processes as membrane protein trafficking, regulating the activity of interacting proteins, and moving such interactors into common microdomains to facilitate interaction (Fouassier et al., *J Biol Chem* 2000 Aug. 11;275 (32):25039–45). Additionally, a human homologue of NHE-RF has been identified as an interactor of merlin, which is a neurofibromatosis 2 tumor suppressor protein; the human NHE-RF may play a critical role in the tumor suppressor functions of merlin (Murthy et al., *J Biol Chem* 1998 Jan. 16;273(3):1273–6).

EBP50 has two PSD-95/DlgA/ZO-1-like (PDZ) domains, which are known to bind integral membrane proteins (Reczek et al., *J Cell Biol* 1997 Oct. 6;139(1):169–79). NHE-RF modulates protein kinase A regulation of sodium-hydrogen exchanger through binding of the PDZ domains. NHE-RF may also bind to the ERM proteins, ezrin, moesin and radixin, via the PDZ domains (Murthy et al., *J Biol Chem* 1998 Jan. 16;273(3):1273–6). Furthermore, EBP50 proteins self-associate with other EBP50 proteins via their PDZ domains, providing enhanced functional capabilities, such as the ability to form multiprotein complexes and regulate membrane transport processes (Fouassier et al., *J Biol Chem* 2000 Aug. 11;275(32):25039–45).

Transporter cofactors, particularly members of the sodium/hydrogen exchanger-regulatory factor subfamily, are a major target for drug action and development. Accordingly, it is valuable to the field of pharmaceutical development to identify and characterize previously unknown transport proteins. The present invention advances the state of the art by providing previously unidentified human transport proteins.

SUMMARY OF THE INVENTION

The present invention is based in part on the identification of amino acid sequences of human transporter cofactor peptides and proteins that are related to the sodium/ hydrogen exchanger-regulatory factor subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate transporter cofactor activity in cells and tissues that express the transporter cofactor. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes.

DESCRIPTION OF THE FIGURE SHEETS

FIG. 1 provides the nucleotide sequence of a cDNA molecule that encodes the transporter cofactor protein of the present invention. In addition structure and functional information is provided, such as ATG start, stop and tissue distribution, where available, that allows one to readily determine specific uses of inventions based on this molecular sequence. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes.

FIG. 2 provides the predicted amino acid sequence of the transporter cofactor of the present invention. In addition structure and functional information such as protein family, function, and modification sites is provided where available, allowing one to readily determine specific uses of inventions based on this molecular sequence.

FIG. 3 provides genomic sequences that span the gene encoding the transporter cofactor protein of the present invention. In addition structure and functional information, such as intron/exon structure, promoter location, etc., is provided where available, allowing one to readily determine specific uses of inventions based on this molecular sequence. As illustrated in FIG. 3, SNPs were identified at 18 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a transporter cofactor protein or part of a transporter cofactor protein and are related to the sodium/hydrogen exchanger-regulatory factor subfamily. Utilizing these sequences, additional genomic sequences were assembled and transcript and/or cDNA sequences were isolated and characterized. Based on this analysis, the present invention provides amino acid sequences of human transporter cofactor peptides and proteins that are related to the sodium/hydrogen exchanger-regulatory factor subfamily, nucleic acid sequences in the form of transcript sequences, cDNA sequences and/or genomic sequences that encode these transporter cofactor peptides and proteins, nucleic acid variation (allelic information), tissue distribution of expression, and information about the closest art known protein/peptide/domain that has structural or sequence homology to the transporter cofactor of the present invention.

In addition to being previously unknown, the peptides that are provided in the present invention are selected based on their ability to be used for the development of commercially important products and services. Specifically, the present peptides are selected based on homology and/or structural relatedness to known transporter cofactor proteins of the sodium/hydrogen exchanger-regulatory factor subfamily and the expression pattern observed. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known sodium/hydrogen exchanger-regulatory factor family or subfamily of transporter cofactor proteins.

Specific Embodiments

Peptide Molecules

The present invention provides nucleic acid sequences that encode protein molecules that have been identified as being members of the transporter cofactor family of proteins and are related to the sodium/hydrogen exchanger-regulatory factor subfamily (protein sequences are provided in FIG. 2, transcript/cDNA sequences are provided in FIGS. 1 and genomic sequences are provided in FIG. 3). The peptide sequences provided in FIG. 2, as well as the obvious variants described herein, particularly allelic variants as identified herein and using the information in FIG. 3, will be referred herein as the transporter cofactor peptides of the present invention, transporter cofactor peptides, or peptides/proteins of the present invention.

The present invention provides isolated peptide and protein molecules that consist of, consist essentially of, or comprising the amino acid sequences of the transporter cofactor peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the transporter cofactor peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated transporter cofactor peptide can be purified from cells that naturally express it, purified from cells that have been altered to express it (recombinant), or synthesized using known protein synthesis methods. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes. For example, a nucleic acid molecule encoding the transporter cofactor peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the transporter cofactor peptides of the present invention are the naturally occurring mature proteins. A brief description of how various types of these proteins can be made/isolated is provided below.

The transporter cofactor peptides of the present invention can be attached to heterologous sequences to form chimeric or fusion proteins. Such chimeric and fusion proteins comprise a transporter cofactor peptide operatively linked to a heterologous protein having an amino acid sequence not substantially homologous to the transporter cofactor peptide. "Operatively linked" indicates that the transporter cofactor peptide and the heterologous protein are fused in-frame. The heterologous protein can be fused to the N-terminus or C-terminus of the transporter cofactor peptide.

In some uses, the fusion protein does not affect the activity of the transporter cofactor peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant transporter cofactor peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al, *Current Protocols in Molecular Biology*, 1992). Moreover, many expression vectors are commercially available that already encode a fusion moiety (e.g., a GST protein). A transporter cofactor peptide-encoding nucleic acid can be cloned into such an expression vector such that the fusion moiety is linked in-frame to the transporter cofactor peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the transporter cofactor peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Hunana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the transporter cofactor peptides of the present invention as well as being encoded by the same genetic locus as the transporter cofactor peptide provided herein. The gene encoding the novel transporter regulatory factor protein of the present invention is located on a genome component that has been mapped to human chromosome 17 (as indicated in FIG. 3), which is supported by multiple lines of evidence, such as STS and BAC map data.

Allelic variants of a transporter cofactor peptide can readily be identified as being a human protein having a high degree (significant) of sequence homology/identity to at least a portion of the transporter cofactor peptide as well as being encoded by the same genetic locus as the transporter cofactor peptide provided herein. Genetic locus can readily be determined based on the genomic information provided in FIG. 3, such as the genomic sequence mapped to the reference human. The gene encoding the novel transporter regulatory factor protein of the present invention is located on a genome component that has been mapped to human chromosome 17 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a transporter cofactor peptide encoding nucleic acid molecule under stringent conditions as more fully described below.

FIG. 3 provides information on SNPs that have been found in the gene encoding the transporter cofactor protein of the present invention. SNPs were identified at 18 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. Positioning of each SNP in exons, introns, or outside the ORF can readily be determined using the DNA positions given for each SNP and the start/stop, exon, and intron genomic coordinates given in FIG. 3.

Paralogs of a transporter cofactor peptide can readily be identified as having some degree of significant sequence homology/identity to at least a portion of the transporter cofactor peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a transporter cofactor peptide encoding nucleic acid molecule under moderate to stringent conditions as more fully described below.

Orthologs of a transporter cofactor peptide can readily be identified as having some degree of significant sequence homology/identity to at least a portion of the transporter cofactor peptide as well as being encoded by a gene from another organism. Preferred orthologs will be isolated from mammals, preferably primates, for the development of human therapeutic targets and agents. Such orthologs will be encoded by a nucleic acid sequence that will hybridize to a transporter cofactor peptide encoding nucleic acid molecule under moderate to stringent conditions, as more fully described below, depending on the degree of relatedness of the two organisms yielding the proteins.

Non-naturally occurring variants of the transporter cofactor peptides of the present invention can readily be generated using recombinant techniques. Such variants include, but are not limited to deletions, additions and substitutions in the amino acid sequence of the transporter cofactor peptide. For example, one class of substitutions are conserved amino acid substitution. Such substitutions are those that substitute a given amino acid in a transporter cofactor peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant transporter cofactor peptides can be fully functional or can lack function in one or more activities, e.g. ability to bind ligand, ability to transport ligand, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as transporter cofactor activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the transporter cofactor peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a transporter cofactor peptide. Such fragments can be chosen based on the ability to retain one or more of the biological activities of the transporter cofactor peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the transporter cofactor peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in transporter cofactor peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of proteins*, B. C. Johnson, Ed., Academic Press, New York 1–12 (1983); Seifter et al. (*Meth. Enzymol.* 182:626–646 (1990)) and Rattan et al. (*Ann. N.Y. Acad. Sci* 663:48–62 (1992)).

Accordingly, the transporter cofactor peptides of the present invention also encompass derivatives or analogs in which a substituted amino acid residue is not one encoded by the genetic code, in which a substituent group is included, in which the mature transporter cofactor peptide is fused with another compound, such as a compound to increase the half-life of the transporter cofactor peptide (for example, polyethylene glycol), or in which the additional amino acids are fused to the mature transporter cofactor peptide, such as a leader or secretory sequence or a sequence for purification of the mature transporter cofactor peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a transporter cofactor-effector protein interaction or transporter cofactor-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, transporter cofactors isolated from humans and their human/mammalian orthologs serve as targets for identifying agents for use in mammalian therapeutic applications, e.g. a human drug, particularly in modulating a biological or pathological response in a cell or tissue that expresses the transporter cofactor. Experimental data as provided in FIG. 1 indicates that the transporter cofactor proteins of the present invention are expressed in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, and Burkitt's lymphoma, as indicated by virtual northern blot analysis. In addition, PCR-based tissue screening panels indicate expression in human leukocytes. A large percentage of pharmaceutical agents are being developed that modulate the activity of transporter cofactor proteins, particularly members of the sodium/hydrogen exchanger-regulatory factor subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes. Such uses can readily be determined using the information provided herein, that known in the art and routine experimentation.

The proteins of the present invention (including variants and fragments that may have been disclosed prior to the present invention) are useful for biological assays related to transporter cofactors that are related to members of the sodium/hydrogen exchanger-regulatory factor subfamily. Such assays involve any of the known transporter cofactor functions or activities or properties useful for diagnosis and treatment of transporter cofactor-related conditions that are specific for the subfamily of transporter cofactors that the one of the present invention belongs to, particularly in cells and tissues that express the transporter cofactor. Experimental data as provided in FIG. 1 indicates that the transporter cofactor proteins of the present invention are expressed in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, and Burkitt's lymphoma, as indicated by virtual northern blot analysis. In addition, PCR-based tissue screening panels indicate expression in human leukocytes. The proteins of the present invention are also useful in drug screening assays, in cell-based or cell-free systems ((Hodgson, Bio/technology, 1992 Sep. 10(9);973–80). Cell-based systems can be native, i.e., cells that normally express the transporter cofactor, as a biopsy or expanded in cell culture. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes. In an alternate embodiment, cell-based assays involve recombinant host cells expressing the transporter cofactor protein.

The polypeptides can be used to identify compounds that modulate transporter cofactor activity of the protein in its natural state or an altered form that causes a specific disease or pathology associated with the transporter cofactor. Both the transporter cofactors of the present invention and appropriate variants and fragments can be used in high-throughput screens to assay candidate compounds for the ability to bind to the transporter cofactor. These compounds can be further screened against a functional transporter cofactor to determine the effect of the compound on the transporter cofactor activity. Further, these compounds can be tested in animal or invertebrate systems to determine activity/effectiveness. Compounds can be identified that activate (agonist) or inactivate (antagonist) the transporter cofactor to a desired degree.

Further, the proteins of the present invention can be used to screen a compound for the ability to stimulate or inhibit interaction between the transporter cofactor protein and a molecule that normally interacts with the transporter cofactor protein, e.g. a substrate or a component of the signal pathway that the transporter cofactor protein normally interacts (for example, a sodium/hydrogen exchanger). Such assays typically include the steps of combining the transporter cofactor protein with a candidate compound under conditions that allow the transporter cofactor protein, or fragment, to interact with the target molecule, and to detect the formation of a complex between the protein and the target or to detect the biochemical consequence of the interaction with the transporter cofactor protein and the target, such as any of the associated effects of signal transduction such as changes in membrane potential, protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, $F(ab')_2$, Fab expression library, fragments, and epitope-binding fragments of antibodies); and 4) small organic and inorganic molecules (e.g., molecules obtained from combinatorial and natural product libraries).

One candidate compound is a soluble fragment of the receptor that competes for ligand binding. Other candidate compounds include mutant transporter cofactors or appropriate fragments containing mutations that affect transporter cofactor function and thus compete for ligand. Accordingly, a fragment that competes for ligand, for example with a higher affinity, or a fragment that binds ligand but does not allow release, is encompassed by the invention.

The invention further includes other end point assays to identify compounds that modulate (stimulate or inhibit) transporter cofactor activity. The assays typically involve an assay of events in the signal transduction pathway that indicate transporter cofactor activity. Thus, the transport of a ligand, change in cell membrane potential, activation of a protein, a change in the expression of genes that are up- or down-regulated in response to the transporter cofactor protein dependent signal cascade can be assayed.

Any of the biological or biochemical functions mediated by the transporter cofactor can be used as an endpoint assay.

These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the transporter cofactor can be assayed. Experimental data as provided in FIG. 1 indicates that the transporter cofactor proteins of the present invention are expressed in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, and Burkitt's lymphoma, as indicated by virtual northern blot analysis. In addition, PCR-based tissue screening panels indicate expression in human leukocytes.

Binding and/or activating compounds can also be screened by using chimeric transporter cofactor proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a ligand-binding region can be used that interacts with a different ligand then that which is recognized by the native transporter cofactor. Accordingly, a different set of signal transduction components is available as an end-point assay for activation. This allows for assays to be performed in other than the specific host cell from which the transporter cofactor is derived.

The proteins of the present invention are also useful in competition binding assays in methods designed to discover compounds that interact with the transporter cofactor (e.g. binding partners and/or ligands). Thus, a compound is exposed to a transporter cofactor polypeptide under conditions that allow the compound to bind or to otherwise interact with the polypeptide. Soluble transporter cofactor polypeptide is also added to the mixture. If the test compound interacts with the soluble transporter cofactor polypeptide, it decreases the amount of complex formed or activity from the transporter cofactor target. This type of assay is particularly useful in cases in which compounds are sought that interact with specific regions of the transporter cofactor. Thus, the soluble polypeptide that competes with the target transporter cofactor region is designed to contain peptide sequences corresponding to the region of interest.

To perform cell free drug screening assays, it is sometimes desirable to immobilize either the transporter cofactor protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of transporter cofactor-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a transporter cofactor-binding protein and a candidate compound are incubated in the transporter cofactor protein-presenting wells and the amount of complex trapped in the well can be quantitated. Methods for detecting such complexes, in addition to those described above for the GST-immobilized complexes, include immunodetection of complexes using antibodies reactive with the transporter cofactor protein target molecule, or which are reactive with transporter cofactor protein and compete with the target molecule, as well as enzyme-linked assays which rely on detecting an enzymatic activity associated with the target molecule.

Agents that modulate one of the transporter cofactors of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of transporter cofactor activity identified according to these drug screening assays can be used to treat a subject with a disorder mediated by the transporter cofactor pathway, by treating cells or tissues that express the transporter cofactor. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes. These methods of treatment include the steps of administering a modulator of transporter cofactor activity in a pharmaceutical composition to a subject in need of such treatment, the modulator being identified as described herein.

In yet another aspect of the invention, the transporter cofactors can be used as "bait proteins" in a two-hybrid assay or three-hybrid assay (see, e.g., U.S. Pat. No. 5,283, 317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the transporter cofactor and are involved in transporter cofactor activity. Such transporter cofactor-binding proteins are also likely to be involved in the propagation of signals by the transporter cofactors or transporter cofactor targets as, for example, downstream elements of a transporter cofactor-mediated signaling pathway. Alternatively, such transporter cofactor-binding proteins are likely to be transporter cofactor inhibitors.

The two-hybrid system is based on the modular nature of most transcription factors, which consist of separable DNA-binding and activation domains. Briefly, the assay utilizes two different DNA constructs. In one construct, the gene that codes for a transporter cofactor protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a transporter cofactor-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the transporter cofactor protein.

This invention further pertains to novel agents identified by the above-described screening assays. Accordingly, it is within the scope of this invention to further use an agent identified as described herein in an appropriate animal model. For example, an agent identified as described herein (e.g., a transporter cofactor-modulating agent, an antisense transporter cofactor nucleic acid molecule, a transporter cofactor-specific antibody, or a transporter cofactor-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The transporter cofactor proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes. The method involves contacting a biological sample with a compound capable of interacting with the transporter cofactor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered transporter cofactor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2): 254–266(1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the transporter cofactor protein in which one or more of the transporter cofactor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and transporter cofactor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes.

Accordingly, methods for treatment include the use of the transporter cofactor protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the transporter cofactor proteins. Antibodies can be prepared from any region of the peptide as described herein. However, preferred regions will include those involved in function/activity and/or transporter cofactor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the transporter cofactor proteins of the present invention are expressed in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, and Burkitt's lymphoma, as indicated by virtual northern blot analysis. In addition, PCR-based tissue screening panels indicate expression in human leukocytes. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes. Thus, where a specific protein has been correlated with expression in a specific tissue, antibodies that are specific for this protein can be used to identify a tissue type.

The antibodies are also useful for inhibiting protein function, for example, blocking the binding of the transporter cofactor peptide to a binding partner such as a ligand or protein binding partner. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a transporter cofactor peptide or protein of the present invention (cDNA, transcript and genomic sequence). Such nucleic acid molecules will consist of, consist essentially of, or comprise a nucleotide sequence that encodes one of the transporter cofactor peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIGS. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIGS. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIGS. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprise several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the transporter cofactor peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the transporter cofactor proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel transporter regulatory factor protein of the present invention is located on a genome component that has been mapped to human chromosome 17 (as indicated in FIG. 3), which is supported by multiple lines of evidence, such as STS and BAC map data.

FIG. 3 provides information on SNPs that have been found in the gene encoding the transporter cofactor protein of the present invention. SNPs were identified at 18 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. Positioning of each SNP in exons, introns, or outside the ORF can readily be determined using the DNA positions given for each SNP and the start/stop, exon, and intron genomic coordinates given in FIG. 3.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6X sodium chloride/sodium citrate (SSC) at about 45° C., followed by one or more washes in 0.2 X SSC, 0.1% SDS at 50–65° C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 18 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel transporter regulatory factor protein of the present invention is located on a genome component that has been mapped to human chromosome 17 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the transporter cofactor proteins of the present invention are expressed in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, and Burkitt's lymphoma, as indicated by virtual northern blot analysis. In addition, PCR-based tissue screening panels indicate expression in human leukocytes.

Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in transporter cofactor protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a transporter cofactor protein, such as by measuring a level of a transporter cofactor-encoding nucleic acid in a sample of cells from a subject e.g., mRNA or genomic DNA, or determining if a transporter cofactor gene has been mutated. Experimental data as provided in FIG. 1 indicates that the transporter cofactor proteins of the present invention are expressed in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, and Burkitt's lymphoma, as indicated by virtual northern blot analysis. In addition, PCR-based tissue screening panels indicate expression in human leukocytes.

Nucleic acid expression assays are useful for drug screening to identify compounds that modulate transporter cofactor nucleic acid expression.

The invention thus provides a method for identifying a compound that can be used to treat a disorder associated with nucleic acid expression of the transporter cofactor gene, particularly biological and pathological processes that are mediated by the transporter cofactor in cells and tissues that express it. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes. The method typically includes assaying the ability of the compound to modulate the expression of the transporter cofactor nucleic acid and thus identifying a compound that can be used to treat a disorder characterized by undesired transporter cofactor nucleic acid expression. The assays can be performed in cell-based and cell-free systems. Cell-based assays include cells naturally expressing the transporter cofactor nucleic acid or recombinant cells genetically engineered to express specific nucleic acid sequences.

The assay for transporter cofactor nucleic acid expression can involve direct assay of nucleic acid levels, such as mRNA levels, or on collateral compounds involved in the signal pathway. Further, the expression of genes that are up- or down-regulated in response to the transporter cofactor signal pathway can also be assayed. In this embodiment the regulatory regions of these genes can be operably linked to a reporter gene such as luciferase.

Thus, modulators of transporter cofactor gene expression can be identified in a method wherein a cell is contacted with a candidate compound and the expression of mRNA determined. The level of expression of transporter cofactor mRNA in the presence of the candidate compound is compared to the level of expression of transporter cofactor mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate transporter cofactor nucleic acid expression in cells and tissues that express the transporter cofactor. Experimental data as provided in FIG. 1 indicates that the transporter cofactor proteins of the present invention are expressed in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, and Burkitt's lymphoma, as indicated by virtual northern blot analysis. In addition, PCR-based tissue screening panels indicate expression in human leukocytes. Modulation includes both up-regulation (i.e. activation or agonization) or down-regulation (suppression or antagonization) or nucleic acid expression.

Alternatively, a modulator for transporter cofactor nucleic acid expression can be a small molecule or drug identified using the screening assays described herein as long as the drug or small molecule inhibits the transporter cofactor nucleic acid expression in the cells and tissues that express the protein. Experimental data as provided in FIG. 1 indicates expression in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, Burkitt's lymphoma, and leukocytes.

The nucleic acid molecules are also useful for monitoring the effectiveness of modulating compounds on the expression or activity of the transporter cofactor gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in transporter cofactor nucleic acid expression, and particularly in qualitative changes that lead to pathology. The nucleic acid molecules can be used to detect mutations in transporter cofactor genes and gene expression products such as mRNA. The nucleic acid molecules can be used as hybridization probes to detect naturally occurring genetic mutations in the transporter cofactor gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the transporter cofactor gene associated with a dysfunction provides a diagnostic tool for an active disease or susceptibility to disease when the disease results from overexpression, underexpression, or altered expression of a transporter cofactor.

Individuals carrying mutations in the transporter cofactor gene can be detected at the nucleic acid level by a variety of techniques. FIG. 3 provides information on SNPs that have been found in the gene encoding the transporter cofactor of the present invention. SNPs were identified at 18 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. Positioning of each SNP in exons, introns, or outside the ORF can readily be determined using the DNA positions given for each SNP and the start/stop, exon, and intron genomic coordinates given in FIG. 3. The gene encoding the novel transporter regulatory factor protein of the present invention is located on a genome component that has been mapped to human chromosome 17 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a transporter cofactor gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant transporter cofactor gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the transporter cofactor gene in an individual in order to select an appropriate compound or dosage regimen for treatment. FIG. 3 provides information on SNPs that have been found in the gene encoding the transporter cofactor protein of the present invention. SNPs were identified at 18 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. Positioning of each SNP in exons, introns, or outside the ORF can readily be determined using the DNA positions given for each SNP and the start/stop, exon, and intron genomic coordinates given in FIG. 3.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control transporter cofactor gene expression in cells, tissues, and organisms. A DNA antisense nucleic acid molecule is designed to be complementary to a region of the gene involved in transcription, preventing transcription and hence production of transporter cofactor protein. An antisense RNA or DNA nucleic acid molecule would hybridize to the mRNA and thus block translation of mRNA into transporter cofactor protein.

Alternatively, a class of antisense molecules can be used to inactivate mRNA in order to decrease expression of transporter cofactor nucleic acid. Accordingly, these molecules can treat a disorder characterized by abnormal or undesired transporter cofactor nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the transporter cofactor protein, such as ligand binding.

The nucleic acid molecules also provide vectors for gene therapy in patients containing cells that are aberrant in transporter cofactor gene expression. Thus, recombinant cells, which include the patient's cells that have been engineered ex vivo and returned to the patient, are introduced into an individual where the cells produce the desired transporter cofactor protein to treat the individual.

The invention also encompasses kits for detecting the presence of a transporter cofactor nucleic acid in a biological sample. Experimental data as provided in FIG. 1 indicates that the transporter cofactor proteins of the present invention are expressed in humans in placenta choriocarcinomas, ovary adenocarcinomas, retinoblastomas of the eye, brain neuroblastomas, endometrium adenocarcinomas, colon, lung small cell carcinomas, T-lymphocytes, ovarian tumors, pheochromocytomas, fetal liver/spleen, and Burkitt's lymphoma, as indicated by virtual northern blot analysis. In addition, PCR-based tissue screening panels indicate expression in human leukocytes. For example, the kit can comprise reagents such as a labeled or labelable nucleic acid or agent capable of detecting transporter cofactor nucleic acid in a biological sample; means for determining the amount of transporter cofactor nucleic acid in the sample; and means for comparing the amount of transporter cofactor nucleic acid in the sample with a standard. The compound or agent can be packaged in a suitable container. The kit can further comprise instructions for using the kit to detect transporter cofactor protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; *Nat. Biotech.* 14:1675–1680) and Schena, M. et al. (1996; *Proc. Natl. Acad. Sci.* 93:10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides that cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the transporter cofactor proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the transporter cofactor gene of the present invention. FIG. 3 provides information on SNPs that have been found in the gene encoding the transporter cofactor protein of the present invention. SNPs were identified at 18 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. Positioning of each SNP in exons, introns, or outside the ORF can readily be determined using the DNA positions given for each SNP and the start/stop, exon, and intron genomic coordinates given in FIG. 3.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol.3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified transporter cofactor gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterotransporter. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al, *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as transporters, appropriate secretion signals are incorporated into the vector. The signal sequence can be endogenous to the peptides or heterologous to these peptides.

Where the peptide is not secreted into the medium, which is typically the case with transporter cofactors, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a transporter cofactor protein or peptide that can be further purified to produce desired amounts of transporter cofactor protein or fragments. Thus, host cells containing expression vectors are useful for peptide production.

Host cells are also useful for conducting cell-based assays involving the transporter cofactor protein or transporter cofactor protein fragments, such as those described above as well as other formats known in the art. Thus, a recombinant host cell expressing a native transporter cofactor protein is useful for assaying compounds that stimulate or inhibit transporter cofactor function.

Host cells are also useful for identifying transporter cofactor mutants in which these functions are affected. If the mutants naturally occur and give rise to a pathology, host cells containing the mutations are useful to assay compounds that have a desired effect on the mutant transporter cofactor protein (for example, stimulating or inhibiting function) which may not be indicated by their effect on the native transporter cofactor protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA that is integrated into the genome of a cell from which a transgenic animal develops and which remains in the genome of the mature animal in one or more cell types or tissues of the transgenic animal. These animals are useful for studying the function of a transporter cofactor and identifying and evaluating modulators of transporter cofactor activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the transporter cofactor nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the transporter cofactor to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, transporter cofactor activation, and signal transduction, may not be evident from in vitro cell-free or cell-based assays. Accordingly, it is useful to provide non-human transgenic animals to assay in vivo transporter cofactor function, including ligand interaction, the effect of specific mutatations on transporter cofactor function and ligand interaction, and the effect of chimeric transporter cofactors. It is also possible to assess the effect of null mutations, that is mutations that substantially or completely eliminate one or more transporter cofactor functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated peptide consisting of an amino acid sequence of SEQ ID NO: 2.

2. An isolated peptide comprising an amino acid sequence of SEQ ID NO: 2.

3. A composition comprising the isolated peptide of claim 1 and a carrier.

4. A composition comprising the isolated peptide of claim 2 and a carrier.

* * * * *

SEQUENCE LISTING

<160> NUMBER OF SEQ ID NOS: 4

<210> SEQ ID NO 1
<211> LENGTH: 1949
<212> TYPE: DNA
<213> ORGANISM: Human

<400> SEQUENCE: 1

| | | | | | |
|---|---|---|---|---|---|
| gtctgtggtc | ctctctcggc | tcctcgcggc | tcgcggcggc | cgacggttcc | tgggacacct | 60 |
| gcttgcttgg | cccgtccggc | ggctcagggc | ttctctgctg | cgctcccggt | tcgctggacg | 120 |
| ggaagaaggg | ctgggccgtc | ccgtcccgtc | cccatcggaa | ccccaagtcg | cgccgctgac | 180 |
| ccgtcgcagg | gcgagatgag | cgcggacgca | gcggccgggg | cgcccctgcc | ccggctctgc | 240 |
| tgcctggaga | agggtccgaa | cggctacggc | ttccacctgc | acggggagaa | gggcaagttg | 300 |
| ggccagtaca | tccggctggt | ggaggtgaac | ggcgaaaacg | tggagaagga | gacccaccag | 360 |
| caggtggtga | gccgcatccg | cgccgcactc | aacgccgtgc | gcctgctggt | ggtcgacccc | 420 |
| gagacggacg | agcagctgca | gaagctcggc | gtccaggtcc | gagaggagct | gctgcgcgcc | 480 |
| caggaagcgc | cggggcaggc | cgagccgccg | gccgccgccg | aggtgcaggg | ggctggcaac | 540 |
| gaaaatgagc | tcgcgaggc | cgacaagagc | cacccggagc | agcgcgagct | tcggcctcgg | 600 |
| ctctgtacca | tgaagaaggg | ccccagtggc | tatggcttca | acctgcacag | cgacaagtcc | 660 |
| aagccaggcc | agttcatccg | gtcagtggac | ccagactccc | cggctgaggc | ttcagggctc | 720 |
| cgggcccagg | atcgcattgt | ggaggtgaac | ggggtctgca | tggagggaa | gcagcatggg | 780 |
| gacgtggtgt | ccgccatcag | ggctggcggg | gacgagacca | gctgctggt | ggtggacagg | 840 |
| gaaactgacg | agttcttcaa | gaaatgcaga | gtgatcccat | ctcaggagca | cctgaatggt | 900 |
| cccctgcctg | tgcccttcac | caatggggag | atacagaagg | agaacagtcg | tgaagccctg | 960 |
| gcagaggcag | ccttggagag | ccccaggcca | gccctggtga | gatccgcctc | cagtgacacc | 1020 |
| agcgaggagc | tgaattccca | agacagcccc | ccaaaacagg | actccacagc | gccctcgtct | 1080 |
| acctcctcct | ccgaccccat | cctagacttc | aacatctccc | tggccatggc | caaagagagg | 1140 |
| gcccaccaga | aacgcagcag | caaacgggcc | ccgcagatgg | actggagcaa | gaaaaacgaa | 1200 |
| ctcttcagca | acctctgagc | gccctgctgc | cacccagtga | ctggcagggc | cgagccagca | 1260 |
| ttccaccca | ccttttcct | tctccccaat | tactcccctg | aatcaatgta | caaatcagca | 1320 |
| cccacatccc | ctttcttgac | aaatgatttt | tctagagaac | tatgttcttc | cctgactta | 1380 |
| gggaaggtga | atgtgttccc | gtcctcccgc | agtcagaaag | gagactctgc | ctccctcctc | 1440 |
| ctcactgagt | gcctcatcct | accgggtgtc | cctttgccac | cctgcctggg | acatcgctgg | 1500 |
| aacctgcacc | atgccaggat | catgggacca | ggcgagaggg | caccctccct | tcctccccca | 1560 |
| tgtgataaat | gggtccaggg | ctgatcaaag | aactctgact | gcagaactgc | cgctctcagt | 1620 |
| ggacagggca | tctgttaccc | tgagacctgt | ggcagacacg | tcttgttttc | atttgatttt | 1680 |
| tgttaagagt | gcagtattgc | agagtctaga | ggaattttg | tttccttgat | taacatgatt | 1740 |
| ttcctggttg | ttacatccag | ggcatggcag | tggcctcagc | cttaaacttt | tgttcctact | 1800 |
| cccaccctca | gcgaactggg | cagcacgggg | agggtttggc | tacccctgcc | catccctgag | 1860 |
| ccaggtacca | ccattgtaag | gaaacacttt | cagaaattca | gctggttcct | ccaaaaaaaa | 1920 |
| aaaaaaaaaa | aaaaaaaaaa | aaaaaaaa | | | | 1949 |

```
<210> SEQ ID NO 2
<211> LENGTH: 340
<212> TYPE: PRT
<213> ORGANISM: Human

<400> SEQUENCE: 2

Met Ser Ala Asp Ala Ala Gly Ala Pro Leu Pro Arg Leu Cys Cys
 1               5                  10                  15

Leu Glu Lys Gly Pro Asn Gly Tyr Gly Phe His Leu His Gly Glu Lys
             20                  25                  30

Gly Lys Leu Gly Gln Tyr Ile Arg Leu Val Glu Val Asn Gly Glu Asn
             35                  40              45

Val Glu Lys Glu Thr His Gln Gln Val Val Ser Arg Ile Arg Ala Ala
 50                      55                  60

Leu Asn Ala Val Arg Leu Val Val Asp Pro Glu Thr Asp Glu Gln
 65                  70                  75                  80

Leu Gln Lys Leu Gly Val Gln Val Arg Glu Glu Leu Leu Arg Ala Gln
                 85                  90                  95

Glu Ala Pro Gly Gln Ala Glu Pro Ala Ala Glu Val Gln Gly
                100                 105                 110

Ala Gly Asn Glu Asn Glu Pro Arg Glu Ala Asp Lys Ser His Pro Glu
             115                 120                 125

Gln Arg Glu Leu Arg Pro Arg Leu Cys Thr Met Lys Lys Gly Pro Ser
     130                 135                 140

Gly Tyr Gly Phe Asn Leu His Ser Asp Lys Ser Lys Pro Gly Gln Phe
145                 150                 155                 160

Ile Arg Ser Val Asp Pro Asp Ser Pro Ala Glu Ala Ser Gly Leu Arg
                 165                 170                 175

Ala Gln Asp Arg Ile Val Glu Val Asn Gly Val Cys Met Glu Gly Lys
             180                 185                 190

Gln His Gly Asp Val Val Ser Ala Ile Arg Ala Gly Gly Asp Glu Thr
     195                 200                 205

Lys Leu Leu Val Val Asp Arg Glu Thr Asp Glu Phe Phe Lys Lys Cys
210                 215                 220

Arg Val Ile Pro Ser Gln Glu His Leu Asn Gly Pro Leu Pro Val Pro
225                 230                 235                 240

Phe Thr Asn Gly Glu Ile Gln Lys Glu Asn Ser Arg Glu Ala Leu Ala
                 245                 250                 255

Glu Ala Ala Leu Glu Ser Pro Arg Pro Ala Leu Val Arg Ser Ala Ser
             260                 265                 270

Ser Asp Thr Ser Glu Glu Leu Asn Ser Gln Asp Ser Pro Pro Lys Gln
     275                 280                 285

Asp Ser Thr Ala Pro Ser Ser Thr Ser Ser Ser Asp Pro Ile Leu Asp
290                 295                 300

Phe Asn Ile Ser Leu Ala Met Ala Lys Glu Arg Ala His Gln Lys Arg
305                 310                 315                 320

Ser Ser Lys Arg Ala Pro Gln Met Asp Trp Ser Lys Lys Asn Glu Leu
                 325                 330                 335

Phe Ser Asn Leu
            340

<210> SEQ ID NO 3
<211> LENGTH: 24707
<212> TYPE: DNA
<213> ORGANISM: Human
```

-continued

```
<400> SEQUENCE: 3
gtgttgtgaa aaaaaagaga atccctggc tcctggagct ggtgggagac aagattaagc      60
aaacctcccc tgacatgtat ccctttgacc ccaagctctg cctcctccct gaccacccat    120
gccctttcct ttaacttctc aaacagatac cagggcctaa actgctttac ctcccctcct    180
actgagtcag gttaggtggt gggaggtcac ccatttccga gttaaaccaa tgcaatatga    240
gtaaaacaaa gtcatgtggg tatgtctggg gtagagagag gggtagcaag ttcatgtgtc    300
ctccttggtc acatatctcc caaagctctg atccctgcca tgggaagtgg acaggaaaca    360
tgaggtcatg acctgcaggc atctttactg cagctctgcc ggcctggagg gggagagggg    420
gaggaagaag tatgcgctgc acatttctga ggctactgca tttgctttca aggcagaaat    480
cttgctctga gcagtcagcg gctccagttt gggcccgata aggaagttct ccgtggcctc    540
cctcaggcag agcagggagg aggctgacat tgccagtctc ttctgggcc caaggcaggt    600 tgcaggagat ccaatcccat agacagctct gggcctcttg catttgagtt tttcagaatt    660
aaactgcagt attttggaaa gcacatcctg tccactgttt ctttgaagtg agtggggggg    720
gggggtcttg ttgaaggaat tgtcattcac tgccaaaatc attccatcct ccttcctcag    780
tgtctgtcct cagatggtca gctccccgct caacagactg tctcccgcct ctgtgaccag    840
cctctctttg gcaagaggga gctagaaggc tttacagtcc taatcatttt tctgttggaa    900
aaaaaaaaaa aaaaccaagg ctcctttccc tgtggcgtgt acccagaggt tgattacctg    960
agtctgtcct gcctctcccc acccaccctc cctagccaaa cgctgctgcc aaagcccacg   1020
ctattgccct agatggcctg tcttcagcgg gctgcccctc gaggtcccag gctctccgcg   1080
gagccctcac cttcccagca gggatcagaa cctgcactcc tctatgcgag tcctgggaca   1140
gcacaaagtg gattagggtt agggttccca caaacggaaa aatgttattc aaacaactct   1200
gtagggtccg aggaggccct ccgtcttaat tctcgagact gaccggccct cgctgccccg   1260
agcgggagca gttgccccgg caacagccgc tccctctcaa ctggagctgc acccaggctt   1320
tggctaaagg ctgttaaaac gttggccagg tgcggaggct cacgtctgta atcccagggc   1380
ggatcacctg aggtcaggag tttgaaacca tcctggccaa catggcgaaa tttcgtctct   1440
actaaaaata caaaaattag cggggcgtgg tggtgcgcgc ctgtaacccc agctgctcgg   1500
gaggctgagg caggggaatc gcttgaaccc gggaggcgga ggttgcagtg atccgagatc   1560
gcgccacggc agtccagcct gggcgacaga gcgagactcc gtctcaaaaa aaaaaaaaa   1620 agttagggtc ctttacccga gggccggctt tcctcactcc ccgccacagg taggggaaac   1680
caggccggag ccggcgggcc caccccgccca gaaccgggaa ttcggcgagc cccgcccctg   1740 ccacccagc gccggccgct cggtaacaaa cacttccact tcctgagcgc tagtcttcgc   1800
ccgccgcggg gcgccgcgcc gagcgcaggc cccgccccgc gcgttcccaa tggccggcgc   1860
cgttcacccg gccggagcgc ccaggcctgc agccccctat tggcccgcgg gaggtccca   1920 ccctcagcgc ggccccgccc ccggggtaag gagccggggc ggactctggg acgctcagac   1980
gccgcgcggg gcgggattg gtctgtgctc ctctctcggc cctcgcggc tcgcggcggc   2040 cgacggttcc tgggacacct gcttgcttgg cccgtccggc ggctcagggc ttctctgctg   2100
cgctcccggt tcgctggacg ggaagaaggg ctgggccgtc ccgtcccgtc cccatcggaa   2160
ccccaagtcg cgccgctgac ccgtcgcagg gcgagatgag cgcggacgca gcggccgggg   2220
cgcccctgcc ccggctctgc tgcctggaga agggtccgaa cggctacggc ttccacctgc   2280
acggggagaa gggcaagttg gccagtaca tccggctggt ggagcccggc tcgccggccg   2340
```

```
agaaggcggg gctgctggcg ggggaccggc tggtggaggt gaacggcgaa aacgtggaga    2400
aggagaccca ccagcaggtg gtgagccgca tccgcgccgc actcaacgcc gtgcgcctgc    2460
tggtggtcga ccccgagacg gacgagcagc tgcagaagct cggcgtccag gtccgagagg    2520
agctgctgcg cgcccaggaa gcgccggggc aggccgagcc gccggccgcc gccgaggtgc    2580 aggggctgg caacgaaaat gagcctcgcg aggccgacaa gagccacccg gagcaggtaa    2640
gcggggcccg agccgcgcag gctggcatgg agtgggagga ggatccggag agacccaggt    2700
gccccggccg tccagccccg cgcccgccgt cgttttctg aaactcgagc tgcgaggggg    2760
agaccgcttc cgcccgccga ccaggcgccc tgacacatcc taggcaggcc tggggctgcg    2820
tcccgcgacc tcctctcctt cccaggctgt gctgggagct gagcgcctt tgccgcctgc    2880 acctcttgtt ccctggcctt tgggagggcg gcgcagggga cccagcccc cttccctcgg    2940 gtctgtgggt gtctgctccc gttcctcgga tcccccaat cctgctcctt ccctggtgcc    3000
ctctcctcgt tcaccccagt ccgcagatgg gccggggaga aagggctctc cgccccagag    3060
gtgccagctt cgcccgccac tcctacttca aaagctagag gaatagcatt actcctcctg    3120
tgtggagccc cggcgcgagg aggccctctc cgcagcccgc cggtgtgtgt cctgaacttc    3180
agtcctgctg gacttcatcc tcccggagtc ctgtgtgact tctaagggag aggaagcccc    3240
accatctcag ggcggtgtgg gggttgcctg gcagggagga ggagccaagg catctcggag    3300
tggtggttct gccacctcag aggatttacg attctcagga atgtgaagag taagcgccta    3360
gaactgtatc tgggagggaa ggggaaagac cttggaagaa gaaaagatg gccatgggga    3420 ggagagagag ctcctggggc tcacggccct gtgtgcgcca gcggagctca cggtgagccg    3480
gtggtcttgc cctggccttg ccatggtcac tctggtgccc acacagccag caggccggtt    3540 gcttttgcc catgtttggt gtttgcccat gggatcccag tttggatcag ctgcaagagg    3600
ggcagctggc aaaataggag ttgtgctgag cctcctgtcc ccagagagtg gagtggtgca    3660
ttgtgtaggg cagggcgtga gcctcccagg acccttcag cttgcaccac cagctctccc    3720
tggtggcagt gtctgatggg agtgtccgtg gggctacgag gagcctcctg gacagagaaa    3780
gggcacagtt cggcattaag gtagaaggca aagccctaga ggatcaactg gtttggtgga    3840
agtgaggtca ccagaagccc tgtccagcca gagctgggtg ctgggaatgc cagggccacc    3900
aggctcccac ttcctgcccc tgccaagctg gcattggcaa ggggaggggg aagggatctg    3960
agcacccgga gcaaggaggt tgatgccagg gagttggggc cgatgatctc cagtcccagg    4020
cagaaatcca gtgtgaactt tgtgctgagt ccatcgatcg atttgacatt cttttttttt    4080
tttttttttg gactttggca cccacacaaa tacccaccca cccccacccc ccacaagttg    4140
cagtctcgtt cagctcctcc cttgccctt ttggttatgc tgctgggtgc cagagggcct    4200
gggaggcgaa cgtggaggcc tggcatagca cacgtgcgca aaggcagcag ctttgagctt    4260
cctgggtgag cacagactca gtattcctgc atgttttgga gggcaccta catttgtgtg    4320 tactttgtta ggccaggaga tgagaggaga gccaccagca aatcctgggg acaccatcac    4380
cagccaagtc ccaggacttc tgagttctgg ttctcccatc tgtgagatgg aggcattggg    4440
cgatgtgatg cctgccttct ctagaattat agaaatgacg tgaagcactt gagcccctta    4500
ctaaatgctg aactgcactc cttcatgcct ggcgtttgaa tcccagctcc tctaaactga    4560
ctcctagtca acaccattga gtccttctag cagaaaatcc tctcctctca atcctgtgtg    4620
ttgagcatac agacacccat gtggttatta gaaaaaatgt taacagacat tgtaagagtt    4680
```

```
cgttttttcta aaacacaccc gtttcctaca taaagcatca aatggaggtt tgccaattcg   4740
ttttagtctg aatttgtgtg caaggtgggg ctgttccctt gtcttcatta gccctccact   4800
tactaagtga tgatatcagt ggaaaagtgt ggcgcagaga gtggttggct gggtggcctc   4860
tggctgggaa gaccagctgt gtccagaacc actcagggca gaggctgagg ggtgcctgta   4920
acactggcca tccccgctgg ggagtctagg cctaaggagg tggaagtggc tctccagctc   4980
tgcccaccgg ctttgctttg tggatggcct tccccgcctg ccccgtgggg agagaggagc   5040
agcaagaccc gccctgctgt tcccctgctt aaagccctcc tcccccccatt caccaccagt   5100 cacaggatga ggcctaaacc cttgagtctg ggttcagagt gccggccggg cagagccgag   5160
ccagctcagc tgtactagcc aggctgtgcg aagccaagtt acctcacctc tgtaagcctc   5220
catttcctct tgtgtaagtt gggggttatg gcagctacct cggaattgca tgaggctgtg   5280
tgtaaagcac gtagctcagt gcctggcact gagtccaggc tcagccagcc tttgcagttg   5340
gtattggaat gaatacatat ttcatagtga tcattgcaca cctatcatgg ggcagctagc   5400
gctgggtcag cctgcctagt tgggcaaatg ccactgtggc caagcctggc acacagtcag   5460
tgcctgatcg atggtcactg tgggttaaga atgatacgtt gtggccaggt gtggtggctc   5520
acacctgtaa tcccagcact ttgggaggcc aaagtgggag gatcgcctga gcccaggagt   5580
ttgagaccag cctaggcaac atgacaagac cctgtctcta ttaaattttt tctttttttt   5640
ttttaagagt tatatgctgt tccatggccc ttctccatct ggcagcctgt tctcaccact   5700
gcctccctac ccccaaaacc acacccaggg tccgaattcc cctctaacct ctaagccttc   5760
acaccctgac acttctgtcc cctcccaggg agcctgtcct taatccagta ggcagagtta   5820
gcatttcctt tccttcactt ttttttgttt tgttttttgtt tttgttttttt ttgagacaga   5880 ttccacccag gctggagtgg tgtcgcaacc tcgcctcgct gcagcctcga cctccagggc   5940
tcaatcgatc ctcccacctc attctcccta gtagctggga ctacaggcat gcaccactat   6000
tcccagctaa ttttttaaatt cttttgtagag atggagtttc accgtgttgc ccaggctggt   6060
cttgaactcc tgggctgagg tgatctgcca gcctcggcct ccgcctcctc tttgtcctta   6120
catcttttat cgctctaaac acacaatatt ttaatcatct gtttgtgacc ttttttctcca   6180 ctacgtggta agcccaaggg catcaactgt ggcctatttg tgtttctatc cccagcgctg   6240
tccttggcac atggtaggga ggctctcaaa aacagttttt gaattaatga atgaatatat   6300
aacaacagtc agggaccttt gtcctcattc agctcatccc gccccgccca gagattggaa   6360
ttccagatag aacctaccca ctcttctttc ttgcctgcta gcagcttcta tttgaaaact   6420
agaaagccaa aagtccaggc tttggggtca gccagatcag tgtttgaatc ccagctctgc   6480
cgtgtgctgg ttctgggatc ctgggagttc attttttccct gcaaccctca gcctccacct   6540
ctgtgaaagg cactgcctgc agggttattg ggaagatttg gtggcatgac aggtttgtaa   6600
atgaaagtgc tagtttgggg tgtttcctgc cagccctgac cctgatccca gagtcagagt   6660
gcaggcaccc cagggagcaa ggtgggtggt ggggcacagt tagctggagg gccatcaacc   6720
tctttcccag ggcgggcggg ccattttaca ccaaccaagt tggagctctg gtagggcaga   6780
acagagcttg agctgctggg tgtttggatt tgaaatggac agggtatgtg attgtttgtg   6840
tgttgggatc tctttctttg ctggcaaaac agtgtagccc ctggttctta ccttcaagct   6900
cctgttaact cagtaattct ggagatgatt ctcttggaga tagatggggg cttcctggcc   6960
gggcgcagtg acttgtgcct gtaatcccat cacttcggga ggctgaggcg ggaggatcgc   7020
ttaagcccag gagtttgaga ccagcctggg caacatagtg agacctcgtc tctaccaaaa   7080
```

-continued

```
aaacagggggagggggtgaatgggggcttccttctcaaggaactccatatgtctagatg      7140
gggtccttctccccttcccagatgtcccatctcaatggtccctgggaaagtggggtggg      7200
aaattaataagaaactcaggccaggcacggtggctcacgcctgtaatcccagcactttgg    7260
gaggccgaggcgggtggatcagttgaggtcaggagttgaggtcaggagttcaagaccagc   7320
ctggccaacatggtaaaaacccatctctactaaaaatacaaaaattagcgaggcgtggtg   7380
gcaggtgcctgtaatcccagctactcgggagtctgaggcaggagaatggcttgaacctgg   7440
gaggtggagttttcagtgagccgagatcgcgccactgcactccagcccgagcagcagagt   7500
gagactcatctccaaaataaaaaaaaagaaagaagaagctcagccgaggtcttgttggt    7560
gctgcaggactctttacagggagaaaccagagctctagacccaataacaaatgttcctc   7620
tgttttcgttgctctaagatagagtggccctacctggaaggaaacaggttgtacagtgc    7680
ctttaggcactctacctatgacataaagatgttgacatgcatttcttctttctttcttt    7740
ctttctttctttttttttttttttttttttcctgagacagtcttgctctgttgcccagg    7800
ctggagtgcagtggtgtgatctcggctcactgcaacctccgtctctcaagttcaagcaat   7860
tgtcctgcctcagccttccatgtagctaggattacaaacacccgccaccacacctgcta   7920
atttttgtattttagtagagacggagttcaccaccggtgccaggctggtggcacctg      7980
tcacaacaccctgctaatttttgtattttttagtagagatgggggtttcaccacattggcca  8040
ggctggtttcaaactcctgacctcaggtaatccacctgcctcggtctcccaaagtgctgg   8100
gattataggcatgagccaccacacccagccaatatgcatttcattgtccccccagacaaat  8160
tagctattgttttctctatttgtaggttgacagtaagtgttcaatacatgatagctact    8220
atttgtgtctagcactgtgctaagtactaaccttgcctgtctcatttaatccacatgacc   8280
accagtgaggcagatattggccccattctctgcctatggaggctgaggcttgatcagtta   8340
aggtggccatggcgggtcccaggactctgagctagcgactcctcccacacagcgcagggg   8400
tgtgtcttggaacccaaccctctgactctagtgcctgcacagccatttggccacatgagt   8460
aggctgtgcttgaagcctgactctgccaggtgtttctgcccatcatattctgagccacag   8520
ctggaccatcacagtggtataaaattcaggctgcttgaactggcttcctgtaaggatccag  8580
ggcttccaggtgctcctgtcctagcagggcatccttgcagtgcctcagcccataagtgg    8640
caggctcctgtccccatcccttctcacgtgatgtgataggtcaatctggaatctggtaac   8700
caagtatctaccccgccctcactcccagaacctgcacagagagcccccctcaagggtg     8760
gtcttcactgttgaccgaagccttcccctcatggtaggacaactcaccatgtccccagac   8820
tcctaggcaatgtttaggtcctaggcctagaaaaggacaagagttacagattccctga    8880
ggtccaggtcacctcggggtggtgtgggaacacacagagaatgctggccaggttcaagtc  8940
ccactcactgctgggtgctgagagctctgaattctccgagacaggctgcagcctctccct  9000
gtgctaaggtcaggggaacagcaatggccaggggtatttagaggagtgtgtttggggcag  9060
tctcaggcagcacaggtctgtgctgtccggcagcagccaccagcttcgcgaggctcccg   9120
ggcactcgagatgtgctggtccacatgcagacgtgctgtgtgtgcaaaatgcacaccaga   9180
ttttgaagccattgtacaaataaaggatgtacaatagctcaattgttaaaaatggatta    9240
cacattgaaatgataatatttgggtacattatgttaaataaaatattcaattctactat    9300
ttttcctgttttttttttttttggaggcagagtctcgctctgttgcccaggctggagtgc  9360
agtggtgcgatctcggctcactgcaagctccacctcccaggttcaagcgattctcctgcc  9420
```

| | |
|---|---|
| tcagcctccc aagtagctgt gcaccaccac gcccagctga tttttgtatt tttcttttt | 9480 |
| agtagagata gggtttcacc atgttgacca ggctggtctc aaactcctgt gctcaagtga | 9540 |
| tccacttgcc tcgtcctccc aaaatgctgg gattacaggc atgagccacc acacctggcc | 9600 |
| tatttttctt ttctttcttt ctttcttttt tttttttttt ttttttttga cacggagcct | 9660 |
| tgctctgtca cccaggctgg agtgcagtgg cgtgatctcg gctcactgca acctccgcct | 9720 |
| cctgggttca agcggttctc gtgcctcagc ctctggagta ctgggacca caggtgtgca | 9780 |
| ccaccacata tgtctaattt tcatatttt agttgagaca gggtttcacc atgttggcca | 9840 |
| tgctggtctt gaactcccga cctcaggtga tccacctgcc ttggcctccc aaaatgctgg | 9900 |
| gattacaagt gtgagccact gcacccggcc tattttcct ttttcaaatg tgatgactag | 9960 |
| aaaatcttac attccacaca tggctggcat tatatatcta ctggacagtg ctgctctgga | 10020 |
| tctgagctca aatcctgcct ttgcccgtca gccatgtgta cttgagcaac tgactccagc | 10080 |
| tttttgaagc tgggtttcct tttctgtgaa atgctggcaa taatactttc cttttaggac | 10140 |
| tataattggc tcttaagaag aaaacacatg taaagagctc ggtgcctaac acatagtagg | 10200 |
| tgttcagtaa atagcagctg ctatttgtta cttcagtgtt gagccccaat ttcacaagct | 10260 |
| ccttgaaggt tcttaatagc cccttgggac aacccctggg ggttaaatct agagacttct | 10320 |
| gggaggaggg tgaggatga ggaaggatgc agcaggaag gcatggggcg gccagccctg | 10380 |
| gatggtgtcc agccgggctg cagcccaggt accagcctgc tccatcccag gcttgcccag | 10440 |
| ccctgcagag acctgagcca gactctgccc cctcttgccc ccgtgggtct ccatggctgg | 10500 |
| cacagggaga agaggttact agccagaagg agaacctgtt tcagacctct gagtcctggg | 10560 |
| ggtgtctgtc agaccagcag acctcacttt agtttgtgtc tccctcctgg ttcccaccct | 10620 |
| accagactcc agggaaagct cttcccactg agaaatagga aggaagagat caagggctag | 10680 |
| gagcagtgag tgactttttt taaaatggac acatccaaca ttcccctgcc gcccgcacag | 10740 |
| acctggaggg atgtggaggg tggaagggg tcccatagag taaaatgagg tgacatcagg | 10800 |
| gccactacgc aggggccag tgacagccaa gccccctgta cctcacctag ggtaaggaga | 10860 |
| agacaccttc tgcctagagg tgtggacact ggctgagtgc ctggagcccc tggtcacttc | 10920 |
| ccagtgcccc caggctgccc gtcacacagc actccaggca gggccagctg tctccatcct | 10980 |
| ggcttccttg aagagctggc accaggccca gccctgtctc cagaatctgg ggaacaaact | 11040 |
| gagctgtctc ccagagcaaa tatggctctt acacccaaca tactcctgac acacacaccc | 11100 |
| cagcccctga gaacagccag ggttccttcc tgcccccgcc gtcctgcccc cttccatcct | 11160 |
| cttgttgggg ctgattttcc tgtattgggc atgggcact ggtcttcttt gcataaacaa | 11220 |
| gagccctggg ctgggggagg ggcagtcttg agaggtgggg ttacctctgt tgttcccctg | 11280 |
| gacacccaag tggtcttcct actcctccag ccccttcct ctgggtcct gagctagctg | 11340 |
| gctcgaagga agcgggctgg gctgtttctg tagggcccat caccatggca tcagccaggg | 11400 |
| aggggctggg cccaatgggg cgttggcccc caggctccca cagccttccc tgaagggagg | 11460 |
| aaggaggagc agggagcggc cctgggcctg ttccccagag acggtcactg ggattagggt | 11520 |
| atcgactttc cccagctttc caggtgactg ctggtggcgc ctattgaatt ccgtgcccgc | 11580 |
| catccgctcc ctggactgcg tgggtggagg tgatggggcg gccacttagg gcgcggtgaa | 11640 |
| gctccctggg ggaaaggaca gatgaaggga ggaagcctga gggtggagga ggccccggga | 11700 |
| gaagggtgtg gggcagctc tccgggcagg gtcttttctg gaaagccagc cagcattttg | 11760 |
| tgaaagtgag agtctccagc ctgtccagcc ctgggtcacc ccggcccagc tgcgctgccc | 11820 |

```
atcggctgca tggcctcatg ttccctcctg ttgattctgg ctctctgcca gtctcctctc   11880
tgagcagatc ctgattttgt cttgaacttg gtctcccag gctgtcgtcg tcactggagg    11940
tcccactttg ccctccggaa ctcactgggg ctatgttcct tttgagtctc ctcctcccac   12000
catgcttcgg acccctctgt agctggctcc tcctaagatc ctgggggcca cacaccaagc   12060
ccaacatgcc tggacgtcac tcccatttat cccctttccc cagaggcaga acccagccct   12120
gccccagctt ggcggtgagg gtccaagagc aatggtggct gagctcggcc aggtacccca   12180
cacctcccca tcttctcctc tcagtgctgg gcctggagac acaggccag gcccacaga     12240
tccccagggg ggctgcccca agggactccc ctgccagccc cagcctccac ccaggctggg   12300
atgggctggc ttgatgggct gactcagcaa ctggcactga cacctcctgg agacagctgg   12360
gaggctcctg ctagggaggg gtgaggagga acaaggctgg tctcccttga agagtgggaa   12420
cccccttcc catgtgaggg gaggaagtct ctagggactt gggaaggagg ctctgcaggt    12480
gcatcggagc tgtctaaatg ctggtggggt ctaccggggg cttcccatct ccttgtccag   12540
ccacccctc aggtcctgga gccgccacag agccacatct agacagaaca gtggagcagg    12600
tcccagtgca ggggaaggaa acagagggca cctgagcccc tcaggctggg taccctgttt   12660
cccccttgaac tgcacgactt ggtgctggca gagcggagca aggctcaaag caggccctgg  12720
agctttggca ccatatgtca ctaggcgagg ggcactgggc tgaagatcag taagggaagc   12780
ccacagcaca gagaccaggg ccagaggatg ggcatcccaa aggcagctag cacagccctg   12840
ccctgccagc cggggggggc gcccagtagc cacctgcccc cagtccagcc atgcccctgc   12900
cctgtcaccc acaccaggct tcatccccca gctcaggctg cagctccagc tgcgagaggc   12960
cctgagcgcc cggaaggaag gctgtggtag gttgtggttt cttcagctcc cagcctacct   13020
ccagcagagg ctgcagccga tgccctggag agagccctg tctgccctct gctgcctgac    13080
tcctgttggg tcctcacctc ccaatgggtt gccccattct ggacttggat ccttaaggag   13140
caccctgcag tgtggtggaa ggaggacagg ttccaagtca gagaccaggg ttggagttct   13200
ggctgtgtga tgtcaggcag tgggctccac atctctgagc ctcagtttcc ccatctcaaa   13260
aacagctgac aagcccagt caggttgtta tgggaaggtt tttgggagcg cagggacggt    13320
ggagggaggt tggaggaggt cactagagct gccccctgcc tgtcctgaga tttcaccctc   13380
cccactttct cagggtgtct ggctgaagca gaaagctgcg cctgtcctgg tgacggcgac   13440
tggtcagact tgtttctgct cacctaggcg gcccggggga gggcctggct gggagctttg   13500
tggagggatt agctctaggg gagaagagcc tcacttactc ccggaacaag atcccacagg   13560
gctgtgggag tgccgggggg tgagcctggg gcaggtgaca gccgaactag ctgggagtgg   13620
gccctgcagt gaggcagggg gtgggccagg gagaacaagg caagaggagc ttcattcagg   13680
gttcctgagc ctttgtgagc cactcacgtt tttaccactc acttaaccgt ctttgttgtt   13740
ggggtgaggg gtcctcgagc ctggatttgg gtatgaaaac ccaggcaaga aagacctgcc   13800
caagccttta aaggaatgca aagtcatcct ctagccaccc ccagagatcg aaaggctggg   13860
gattgagtct cctgcagatg gtggcggcct cctggggctg gcaagttggg acagaggccc   13920
ataagccctc ctgggcgcgc cttcccaccc ctctcggccc tctccactcc cagctgggga   13980
tttgggtttc agagcagcct ggcacacaca ccccaccccc accagaatct cactcccagc   14040
ttcctatgac tattcattag tattcacaac aatgggaaag tctgggtgtg cacagggatt   14100
ttttacagtt agaaagtgtt taagtcaatg acctcactgg gcctcagcaa ccctgggagg   14160
```

```
cagatggcag tcagaatgat ccataaatga cctgccccag gtcacacagc tcctaaacag   14220
gggagctgga acctggctgg gagccttgac tatccactgc tcattgtctg atgtgctgag   14280
tgataacaca gggccagcag gctggacagc agccagtggc cctgcaccag gcctggagga   14340
gggggagagg gacagggact caggcgtagt ccttgggcac aggcttcggc tgcctacacc   14400
catattccct ccatcatact gtgtgtccag gcctgcagct tctaagctga gctgcttact   14460
ttggaccaag catgttggaa actgttttca gctgagtcca agcactcgaa atctgcgtgt   14520
gcccttttag taggtcacac cctccaggcc acagccacac tgggctccct ttagcccagc   14580
cctgcttttc ccagtcccct ccccattcag gctcctctgt ttctggggtc tctgtgcttc   14640
cgttgccacc tctgcccttg ggcagcggtg tcggggagg aggtcctgga acgcctgagg    14700
atggccccgt cttgtccagg tccccttgct gtgctgaaca ataagttttt ggttatctgc   14760
tccttctggc tcccttttgg ctgggccatt cggcttggtg ggggtgagag agagttcgag   14820
tatatggagg aaggctttac tgtaaacaca ctgaccagct tcagtaaac acctgcctct    14880 tcctcccctg ctgcagagaa cggggtacaa aggggctggg ggtcctcagt catatgcccc   14940
aggtccccag ccaggctgac gggtgccaca ctctgcccc tctccaggag gccagactg     15000 agccaccaat ggggagggat agaggcccga tcaacacagc atgtgattca ccttagactg   15060
tcagaaggga caggcatgtg agagctaacc tggtcctacc cctcatttgg cagaagagga   15120
aactgaggct tggacagagc agtgttttat ccacatcacc taagcagtta gctgcggtgc   15180
tgggtatcca cacaagtctt ttgagtcctg ggccagaacc ctctcaaatt gctgtgtagg   15240
gatctaggca aatttgcatc ctcccaaacc ttccttggtt ggggagatgg ggacaggcag   15300
aggacaggga aggcagaacc tggggcactg tggaatagcc atggaccctc ccctgtccct   15360
gcagcgcgag cttcggcctc ggctctgtac catgaagaag gccccagtg gctatggctt    15420 caacctgcac agcgacaagt ccaagccagg ccagttcatc cggtcagtgg acccagactc   15480
cccggctgag gcttcagggc tccgggccca ggatcgcatt gtggaggtga tgcttctcgc   15540
tctcttccta tctgactgcc ccacccccct gcagatcagc agcacctggg gcagccatca   15600
taccatcatg ggcttgatta gcccacgggc atagccaacc tggagctgct ggatggatgg   15660
gtggatggga gggagggagg gaagggtggt ggatggatag acggaaggac agatggactg   15720
actgatggac tcttctctta cctccactcc cctgggactc ctccttgcca agcagataca   15780
gtgggcagcc tgtgattcac ccatcgatca ggggagatgt ctggggccat ctccaggagc   15840
ttccctgctg ccaggcacac agagtggggt ggcagtaaca aaacccctct cctgagttag   15900
gcctttattt atttagtttt tttttttttt aaatggagtc tcgctttgtt gcccaggctg   15960
ggggagtgca gtggcacaat cccagctcac tgcaacctcc gcctcctggg ttcaagcgat   16020
tctcctgcct cagcctcctg agtagctggg attacaggtg cccaccacca cgcctggcta   16080
atgtttgcat ttttagtaga gacaggattt caccatgttg gccaggctgg tctcaaactc   16140
ctgacctcaa gtgatctgcc cgcctcggcc tcccaaagtg ctgggattcc aggcgtgagc   16200
cacctcaccc ggccccgagt taggcttttta gactcgtgca ttcagggctc tggtgctgtg   16260
ctcctgggag aggaaacgtg aaccaaatgc tcaggcaggt cccagaatca cagtcttaga   16320
acctagagag tagagatcag ctctcccaag acttctcatt ttacacgtga gaaaaccaag   16380
gcccagagaa ggaagtcgga cagcaagtcc ttacccaggc tgggccccac cccggcctcc   16440
cagctcgctc ccatcccatc tctcccagct gtgtttgttt agtctcgtct ggatattttc   16500
gttggccctt cccatgtatc ctgcctcccc agctgactgt caatgggagg accccagcc    16560
```

```
tagttcagga ctctgcagaa atggcggggg tcagtatccc caggttgtga actgcaaact  16620
ggctgagaac caaggtggtc acccctgccc ccaacccccc tccacttacc tgccccagaa  16680
ccaaggcctg tgtccgtaac gcctccccga ccctgccctg caggtgaacg gggtctgcat  16740 ggagggaag cagcatgggg acgtggtgtc cgccatcagg gctggcgggg acgagaccaa  16800
gctgctggtg gtggacaggg aaactgacga gttcttcaag aaatgcagag tgatcccatc  16860
tcaggagcac ctgaatggta agccaggtgg ggccactggc cgtcctgggg ctggagcccc  16920
ccaagtcagg gatgtgagcc agggctaaga ctgctgggtc ccaggcgagg ggtgggcagc  16980
ttcccggcat gggtgctccc tcctcctcct tcatgggagg cccagaggtg tgggctgggg  17040
gagcgggggc ctagtgtagg gagtggcagt gggtttctga ggacggcttg tgatggggtc  17100
agctggcatg aggtcggtga gagagatgga cagatcttct tattcccggc caaagctgca  17160
gccccaaagg aggcccaagc ccccagtcct gtccccacca gcagactttc agggcagtgt  17220
caatgtgagg aaaggggttaa ctccggggag gcctccagcc tttgcttggt cagatcagag  17280
tccagtgacg ggggccggtg cctcccccctc cctcctctca ggttgtcttg gaaactcagc  17340
cttgctggct ctagagagta gtgggtcccc cttcaatccc tgggcccctg ccctccccat  17400
cccccaccat caccctgcca gcctggcgc ctccccctgc ccaggcccga gccaaacagg  17460
gcagggctgc tgcaccgggg cagggagggg ttaagcatgc tctgctcctt ggtctggact  17520
ttctccctgg gaagatggct ccctggagcg ggcaggggtg ctcactgggc catactgagg  17580
gtggaacctc ttgggactttt gcagtgggtg gggcctcctg gagactcaag gttgtatgtg  17640
taaaaggaga ttcacacaaa ggtcctgcga ctcccatcgc cagctgcaag ggcccactgg  17700
ggaggccctg tccccttctg gcgcaatcca aggcctgagg ctcctagaag aggggatggc  17760
ccctggaagt ccctagctgg ctctgggcat gggaggtggg gtaccgcctt acccttatct  17820
cccaagttca tggaaaccag gtaactcaga taatccccctt ctccactgag ggggagacta  17880
aggcccagag aagccccagc cttcctccta gggatctgat acgaggaaga cacagctgga  17940
atctggattc cactcagctc ctgggatact gtccccctgct tcccccaccc cttcaccctg  18000
caggtaattg gccccctcag acattcctcc ctcttctgcc tgtctctcgg gctagagggg  18060
ctgcagcctc tggccaaagg acctgaagag ggagaggcct ggggacagtc ccctccccgc  18120
agtccctcca ggatggcatc ctcacccttt ccatagggag gaatgccccc ctctccggct  18180 gccaggggttt caccctgacc actgtgagct gatggggagg ggacagtgag tgaccctgtg  18240
tcccagcagc ctgtccttgc ccggggaagg ctgtgggtgt caaaagggag gagaagatga  18300
gagtcaggta tctctggctg tgtcctggac tggggacagg gaaaagataa ccaggaattt  18360
taagctaaga gttcagaaga agccctacac tgaccagtcc ctggagatgg aacagccacc  18420
cctgaagcca tgtgggaccc ctaccctgag tgagcccagt gaaggtgacc ccagacctgt  18480
cttctctccc tctgaccccc ccaggtttcc cactggctgg gggagggat acccaggaca  18540 caccccttga gccttctcgt ccccctcat ttcctgattg gcaaatagga gttgggatta  18600
ttttctcttt ttttctttttt cttttctttt tttttgagat ggagtcctgc tctgtcaccc  18660
aggctggagt gcagtggtgc gatctcggct cacagcaaca tctgccccta gattcaagtg  18720
attcttctgc ctcagtctcc tgagtagccg ggactacagc catgcgccac cacgcccagc  18780
aaatttttat attttttagta gagatggggt ttcactatgt tggccaggat ggtctcgatc  18840
tcttgacctt gtgatccgcc cacctcggcc tcccaaagta ctgcgattac aagtgtgagc  18900
```

```
caccgcgcct ggcctttttt ttttttttc cggacacagt ctctgtcacc caggctagag    18960
tgcaatggca caatcttggc tcactgcaac ctccacctcc tggttcaag caattctcct    19020
gcctcagcct cctgagtagc tgggattaca ggcgcctgcc accatgcccg gctaattttt   19080
gtattttag tagggatagg gtttcgccat gttggccagg ctggtcttga actcctgacc    19140
tcaggtgatc cgcctgccac agtctcccaa agtgctgggg tcccagtcat gagccaccga   19200
gcccagacta ttttctcttt cagttgaggc aggtactaac tatagtctgg ggtgtggttc   19260
caattttggt gtcatcatca tcacctggga agcgtttgga aaatgttgat tcttaggcct   19320
gcccactaaa ccagaatctg tgctgccaag gtccaggaat ctgtacttta acaagcttcc   19380
cacgtaggag ttcccaggta ggaattccca ggtaggaatt aggcagccat cctcgaattt   19440
catccccatc tgagacaata cattttttaa acaccttgtg acccatcagt gcctcataag   19500
atcaatttag tagatagaga ccagcaggtt ttttggtttg ttttttttgt tttgttttgt   19560
tttgttttgt tttgccagag tcttgctgtg ttgcccaggc tggagtgtag tggcgtgatc   19620
tcggctcact gcaacctcca ccttctgggt tcaaacaatt ttcccacctc agcctcccaa   19680
gtagctagga ttacaggcgt gtgccaccat gcccagctaa ttttcttttt gtcttttta   19740
gtagagacgg ggtttcacca tgttggccag gctggtctca aactcctaac ctcaagtgat   19800
ccaggtgccc tcgcctccc aaagtgctgg gattactggt gtgagccact atgcctggcc   19860
cagacatttt tttgttttt taatgaatg aaattaaaaa tatcaaagaa cactgtagta   19920
agggtgttgc tttgtgaaac ttttatcaca caaaatcttt gtgtgtgctg agtcatcaaa   19980
atggcaaacg taggccagac atttgctcac acctgtaatc ccaacacttt gggaggccaa   20040
ggtggaagga ttgcttgggg ctaggagttt gagaccatcc tgcatgacat ggcaaggccc   20100
catctctata aaaaaaaaat ttttttaaa taaataaggc aaatgtattc atggtgggtg   20160
gtagtcaaaa aagtttgaga tgttgaccca gggaacaaga tctaataatc tgcccaaacc   20220
caactcctac ctcctctcca cgctctattc catccccgtt ctggactcac ctctgctctg   20280
tcctttgcct aggtccctg cctgtgccct tcaccaatgg ggagatacag aaggtaaggg   20340
cgggtcccct gtctctttgg atttcaatcc ttggggtgca tgagacagat cagaaggtgc   20400
tgtggttggt aggatagcca tctgactaag gccaaaaccc cagggtcccc agttccagct   20460
ccttcttcag ctccaagcta tagaactgcc agaaccctct tggcctctgc ctggggccaa   20520
agctgtcagg agggagcggg ctggctgggc ccctctgcag cccgccatcc tgggtgacaa   20580
gcccccgcct ccaactcccc accatacaga agggccatt cttcccccca agaacagagc    20640
ttcagtgtct ggccacgggc agccgggccc ctgctacttc tagtctgggt tggaagaaca   20700
aagcccctcc tcccccttc cctgggcaga agggaaaggg ggtgaggccc ggggaagaga   20760
tggtggggct gggcgccagc tgaagccatg gaggaaccca ggaagggggct gggtgccaag  20820
ctgacgcccc agccaaagcc ttcgctctgg acaggccga ctcagtcagg ccacagagca    20880
ggaactctgc agggtctgct taaaggttcc ccttccctag gagctcctgc cagggtactt   20940
ggcaaggggg agggccttg gacccagccc tcaaccttct ttcacctcat ctttggatct    21000
agaactttcc atccaccttc ttctttcaag gccctccttt gctgcttcag ggttagggtt   21060
tcaggattcc tggggtcaaa tcctggcaaa cagtcaggtg gaccacatga gattcaggga   21120
gcaccacatg ggctccccat gccccatgt gtccccacat tccaagaagc ccctccctgg   21180
tcactggccc aaaaggcaag ccagtaccta aagccacat tggagtggcc cagggagagg   21240
gagcggttca gctaatccca tgatggtctg ttcccatccc atccctccag cctgagcagt   21300
```

```
agaaccagcc tgccctctga tccccaaagg aatgtaaaaa ggagcccag  caggctcagg   21360
aggtgggaac caggggtggg tggccagggc atcagtgcta cctcttctca gtctgaggcc   21420
cctacttccc caggagctcc ctccctcctc aggacccct  cacccatcc  tctgacaacc   21480
cacaaccctc tcctctctgc caggagaaca gtcgtgaagc cctggcagag gcagccttgg   21540
agagccccag gccagccctg gtgagatccg cctccagtga caccagcgag gaggtaggcc   21600
agccatgcgg ggggtggcaa ctgggttaca ggaagccgat tcccaggccc cacttgttcc   21660
tggcacacca gcctgccttt gaggtcacat gctgagccgc attctgttct tgtgacctgg   21720
cttccctggg cacggcccca acggagccac ctcaccaagg ctgaggacca gggagcctaa   21780
tgagggactg actcccaact tcctgccccc acttctcttt acagctgaat cccaagaca   21840
gcccccaaa  acaggactcc acagcgccct cgtctacctc ctcctccgac cccatcctag   21900
acttcaacat ctccctggcc atggccaaag agagggccca ccagaaacgc agcagcaaac   21960
gggccccgca gatggactgg agcaagaaaa acgaactctt cagcaacctc tgagcgccct   22020
gctgccaccc agtgactggc agggccgagc cagcattcca ccccacctt  ttccttctcc   22080
ccaattactc ccctgaatca atgtacaaat cagcacccac atcccttc   ttgacaaatg   22140
atttttctag agaactatgt tcttccctga ctttagggaa ggtgaatgtg ttcccgtcct   22200
cccgcagtca gaaaggagac tctgcctccc tcctcctcac tgagtgcctc atcctaccgg   22260
gtgtccctt  gccaccctgc ctgggacatc gctggaacct gcaccatgcc aggatcatgg   22320
gaccaggcga gagggcaccc tcccttcctc ccccatgtga taaatgggtc cagggctgat   22380
caaagaactc tgactgcaga actgccgctc tcagtggaca gggcatctgt taccctgaga   22440
cctgtggcag acacgtcttg ttttcatttg attttttgtta agagtgcagt attgcagagt   22500
ctagaggaat ttttgtttcc ttgattaaca tgattttcct ggttgttaca tccagggcat   22560
ggcagtggcc tcagccttaa acttttgttc ctactcccac cctcagcgaa ctgggcagca   22620
cggggagggt ttggctaccc ctgcccatcc ctgagccagg taccaccatt gtaaggaaac   22680
actttcagaa attcagctgg ttcctccaaa cccttcagcc tccgtgtgtt ccttggaagt   22740
tttgtcctct ggccttggac cccttatagg tagaaattga gaaatggtaa gccaaggtgg   22800
tctttggctg ggagggtggg gtacactgga gggagggcca tcaagggctc cctgtgaccc   22860
caagcctggg tagctttagc tagagggcct agctgcagtc ctgtaggaag gaagatgcat   22920
gcacccagcc gggtattcag cttggtgtgg tcagtgtgcc tgtgtgctgg gctgcaagca   22980
ccgattgtgg gctggggacc ccttgtctaa cggggatatt tacaagggga agtgggagct   23040
cagaccaacg ttctcagagg actctgggag gttcctttaa ttccagaagc gtggaaagtg   23100
tgtcccagga tggagctggg tttggaatgt gaggacttgg ctttactctt tctgcctata   23160
gccagtgggg tgcagaattc ccaggggcag gctgggctgg tgccagatcc tctatcttat   23220
ctggccattg tgacctgatt ggagggcaag tgtccagtgc caggggaaaa caaaccggtc   23280
cactgagccc ggggacatgc tgtgtggcta gctggggtgg aagggactgt tcaagggcaa   23340
ggtgccctgc ccccaacaaa agacccaggt ccctgatacc tttggcacct gaagcctgat   23400
ctggaggtcc aggaaggtgg cttgcaagag ctaggctgca gagccgggag gttccgggca   23460
ggtgctcagg aggaaggtgc ccccaggcta gtctccaccc aacccaaagg gacacctctc   23520
agaaaatagg ctcctgggct gagggaatg  agtaaagcag gtagatctgg aatcagggag   23580
tggacagtgt cccccaggcc agtcactatc tggccatctc ctgctccttg tcagaggaac   23640
```

-continued

```
catccaaaac ccttaccaca gcagtgccct gctcagctga cctgccccca ccccaccctt    23700
gcttctaccc tttggcccct gacagattcc cctccacagg ggtcgtggag ggcccctccc    23760
tatctcacct gctgggtggg gaagccctgg gggacctttg actcttcatt aacctgaaga    23820
ctggtggaag gaatgggtgg ccccaaggga actctcattg ctgaggtaca catggtacga    23880
agggagccac ggcaagcaac gcgttcgttt tataatgttt gttttatact gaggcatgtt    23940
ttcggttcca gttgttcaca tgcagtctgc tgtgagactc caagatcaag ggtgctggga    24000
ggccttaggc aagtcacctt acttatctaa gactgtttcc ccacctggaa gatgccctac    24060
aagcctcctg tggctgtgtt tagaaagcat gcccggcctt tcttgacagc cagccacccc    24120
agatgatggc agggcaagga agactgttag gagtcagagt gctcccctca ggtggaagga    24180
aactgggcca actctacttt gtaagccata gggtgccagg tagcccggcc accctgagcc    24240
tgtgcctcca ctgcccccgc gtggccagtc aggtgcagct gctcccagag atggagggtg    24300
aggaacagac gtgggagcac cagagggaca gagctgatgg cctgacgctc tcttcaggag    24360
ggcaccccca aggggcctct gcttcctcag tgcccctga gctttatcag cagagggtg     24420
ttttccagcc acaaggagct gtatctaaca ctaatgcctt taaactcaag actggctcca    24480
ggagagagga ggacggacac taggttgagg ggccaggcca cactcactct ggaccacctg    24540
ttgttcccgg gtcaagttcc cagggtcaca ccagcctgcc tctgcaggac aagaggacca    24600
agctgccctt gagtggacac tgtgaggctg gggcttgtgg tagctcttca cacggaccaa    24660
acgggaaaat caggaaagct ggtagtgcct ggagcttcac tcccagc                  24707
```

<210> SEQ ID NO 4
<211> LENGTH: 358
<212> TYPE: PRT
<213> ORGANISM: Human

<400> SEQUENCE: 4

```
Met Ser Ala Asp Ala Ala Gly Ala Pro Leu Pro Arg Leu Cys Cys
 1               5                  10                  15

Leu Glu Lys Gly Pro Asn Gly Tyr Gly Phe His Leu His Gly Glu Lys
            20                  25                  30

Gly Lys Leu Gly Gln Tyr Ile Arg Leu Val Glu Pro Gly Ser Pro Ala
        35                  40                  45

Glu Lys Ala Gly Leu Leu Ala Gly Asp Arg Leu Val Glu Val Asn Gly
    50                  55                  60

Glu Asn Val Glu Lys Glu Thr His Gln Gln Val Val Ser Arg Ile Arg
65                  70                  75                  80

Ala Ala Leu Asn Ala Val Arg Leu Leu Val Val Asp Pro Glu Thr Asp
                85                  90                  95

Glu Gln Leu Gln Lys Leu Gly Val Gln Val Arg Glu Glu Leu Leu Arg
            100                 105                 110

Ala Gln Glu Ala Pro Gly Gln Ala Glu Pro Pro Ala Ala Glu Val
        115                 120                 125

Gln Gly Ala Gly Asn Glu Asn Glu Pro Arg Glu Ala Asp Lys Ser His
    130                 135                 140

Pro Glu Gln Arg Glu Leu Arg Pro Arg Leu Cys Thr Met Lys Lys Gly
145                 150                 155                 160

Pro Ser Gly Tyr Gly Phe Asn Leu His Ser Asp Lys Ser Lys Pro Gly
                165                 170                 175

Gln Phe Ile Arg Ser Val Asp Pro Asp Ser Pro Ala Glu Ala Ser Gly
            180                 185                 190
```

-continued

```
Leu Arg Ala Gln Asp Arg Ile Val Glu Val Asn Gly Val Cys Met Glu
        195                 200                 205
Gly Lys Gln His Gly Asp Val Val Ser Ala Ile Arg Ala Gly Gly Asp
    210                 215                 220
Glu Thr Lys Leu Leu Val Val Asp Arg Glu Thr Asp Glu Phe Phe Lys
225                 230                 235                 240
Lys Cys Arg Val Ile Pro Ser Gln Glu His Leu Asn Gly Pro Leu Pro
                245                 250                 255
Val Pro Phe Thr Asn Gly Glu Ile Gln Lys Glu Asn Ser Arg Glu Ala
            260                 265                 270
Leu Ala Glu Ala Ala Leu Glu Ser Pro Arg Pro Ala Leu Val Arg Ser
        275                 280                 285
Ala Ser Ser Asp Thr Ser Glu Glu Leu Asn Ser Gln Asp Ser Pro Pro
    290                 295                 300
Lys Gln Asp Ser Thr Ala Pro Ser Ser Thr Ser Ser Ser Asp Pro Ile
305                 310                 315                 320
Leu Asp Phe Asn Ile Ser Leu Ala Met Ala Lys Glu Arg Ala His Gln
                325                 330                 335
Lys Arg Ser Ser Lys Arg Ala Pro Gln Met Asp Trp Ser Lys Lys Asn
            340                 345                 350
Glu Leu Phe Ser Asn Leu
        355
```